United States Patent
Hansen et al.

(10) Patent No.: US 10,040,867 B2
(45) Date of Patent: Aug. 7, 2018

(54) CELL PENETRATING ANTI-GUANOSINE ANTIBODY BASED THERAPY FOR CANCERS WITH RAS MUTATIONS

(71) Applicants: Yale University, New Haven, CT (US); The United States of America as represented by The Department of Veterans Affairs, Washington, DC (US)

(72) Inventors: James E. Hansen, Guilford, CT (US); Richard H. Weisbart, Los Angeles, CA (US); Melissa Young, New Haven, CT (US); Philip W. Noble, New Haven, CT (US)

(73) Assignees: Yale University, New Haven, CT (US); The United States of America, as Represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/123,195

(22) PCT Filed: Mar. 4, 2015

(86) PCT No.: PCT/US2015/018729
§ 371 (c)(1),
(2) Date: Sep. 1, 2016

(87) PCT Pub. No.: WO2015/134607
PCT Pub. Date: Sep. 11, 2015

(65) Prior Publication Data
US 2017/0073429 A1    Mar. 16, 2017

Related U.S. Application Data

(60) Provisional application No. 61/947,492, filed on Mar. 4, 2014.

(51) Int. Cl.
| | | |
|---|---|---|
| *C07K 16/40* | (2006.01) | |
| *C07K 16/30* | (2006.01) | |
| *C07K 16/44* | (2006.01) | |
| *A61K 39/395* | (2006.01) | |
| *A61K 45/06* | (2006.01) | |

(52) U.S. Cl.
CPC ........ *C07K 16/40* (2013.01); *A61K 39/39558* (2013.01); *A61K 45/06* (2013.01); *C07K 16/30* (2013.01); *C07K 16/44* (2013.01); *C07K 2317/24* (2013.01); *C07K 2317/565* (2013.01); *C07K 2317/567* (2013.01); *C07K 2317/622* (2013.01); *C07K 2317/73* (2013.01); *C07K 2317/77* (2013.01); *C07K 2317/82* (2013.01)

(58) Field of Classification Search
None
See application file for complete search history.

(56) References Cited

U.S. PATENT DOCUMENTS

| | | |
|---|---|---|
| 4,812,397 A | 3/1989 | Weisbart |
| 5,780,033 A | 7/1998 | Torchilin |
| 7,189,396 B1* | 3/2007 | Weisbart ................ C07K 16/18 424/133.1 |
| 9,701,740 B2 | 7/2017 | Hansen et al. |
| 2002/0090608 A1 | 7/2002 | Palese |
| 2003/0083305 A1 | 5/2003 | Palese |
| 2003/0109475 A1 | 6/2003 | Debs |
| 2004/0033235 A1 | 2/2004 | Bolognesi |
| 2004/0052820 A1 | 3/2004 | Bolognesi |
| 2005/0003343 A1 | 1/2005 | Palese |
| 2005/0221400 A1* | 10/2005 | Gudas ................ A61K 39/0011 435/7.23 |
| 2005/0256073 A1 | 11/2005 | Lipford |
| 2006/0110740 A1 | 5/2006 | Hurwitz |
| 2006/0216701 A1 | 9/2006 | Palese |
| 2006/0263367 A1 | 11/2006 | Fey |
| 2008/0004561 A1 | 1/2008 | Genkin |
| 2008/0292618 A1 | 11/2008 | Weisbart |
| 2009/0028901 A1 | 1/2009 | Palese |
| 2009/0186337 A1 | 7/2009 | Eleouet |
| 2009/0186802 A1 | 7/2009 | Alluis |
| 2010/0143358 A1 | 6/2010 | Weisbart |
| 2010/0196993 A1 | 8/2010 | Nishimura |
| 2010/0311171 A1 | 12/2010 | Nakanishi |
| 2011/0300164 A1 | 12/2011 | Lipford |
| 2012/0010124 A9 | 1/2012 | Alluis |

(Continued)

FOREIGN PATENT DOCUMENTS

| | | |
|---|---|---|
| EP | 1666055 | 6/2006 |
| WO | 9732602 | 9/1997 |

(Continued)

OTHER PUBLICATIONS

Colburn et al. (Clinica Chimica Acta, 370: 9-16, 2007).*
Skoulidis et al. (Cancer Cell, 18: 499-509, 2010).*
Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Berglund, et al., "The epitope space of the human proteome", Protein Sci., 17:606-13 (2008).
Corada, et al., "Monoclonal antibodies directed to different regions of vascular endothelial cadherin extracellular domain affect adhesion and clustering of the protein and modulate endothelial permeability", Blood, 97(6):1679-84 (2001).

(Continued)

*Primary Examiner* — Nelson B Moseley, II
(74) *Attorney, Agent, or Firm* — Pabst Patent Group LLP

(57) ABSTRACT

It has been established that cancer cells with oncogenic mutants in the small GTPase K-Ras are susceptible to antibodies that bind intracellular guanosine, but delivery of antibodies into cells can be challenging. A subset of lupus autoantibodies is associated with anti-guanosine activity, and is capable of cellular penetration. These antibodies have potential as therapeutic agents targeted towards K-Ras associated malignancies.

35 Claims, 2 Drawing Sheets

(56) References Cited

U.S. PATENT DOCUMENTS

| | | | |
|---|---|---|---|
| 2012/0214240 A1 | 8/2012 | Nakanishi |
| 2013/0137644 A1 | 5/2013 | Alluis |
| 2013/0266570 A1 | 10/2013 | Weisbart |
| 2014/0050723 A1 | 2/2014 | Hansen |
| 2014/0234309 A1 | 8/2014 | Nishimura |
| 2015/0376279 A1 | 12/2015 | Hansen |
| 2016/0235859 A1 | 8/2016 | Weisbart |
| 2017/0291961 A1 | 10/2017 | Hansen |

FOREIGN PATENT DOCUMENTS

| | | |
|---|---|---|
| WO | 008091911 | 7/2008 |
| WO | 2009134027 | 11/2009 |
| WO | 2012135831 | 10/2012 |
| WO | 2012145125 | 10/2012 |
| WO | 2015106290 | 7/2015 |
| WO | 015134607 | 9/2015 |
| WO | 016033321 | 3/2016 |
| WO | 016033324 | 3/2016 |

OTHER PUBLICATIONS

Eivazova, et al., "Specificity and binding kinetics of murine lupus anti-DNA monoclonal antibodies implicate different stimuli for their production", Immunology, 101:371-7 (2000).
Kulkarin-Kale, et al., "CEP: a conformational epitope prediction server", Nucleic Acids Res., 33:W168-W171 (2005).
Padlan, "X-ray crystallography of anti-bodies", Adv Protein Chem., 49:57-133 (1996).
Rivadeneyra-Espinoza, et al., "Cell-penetrating anti-native DNA antibodies trigger apoptosis through both the neglect and programmed pathways", J Auto Immunity, 26:52-6 (2006).
Tzartos, et al., "Epitope mapping by antibody completion", Methods Molecular Biol., 66:55-66 (1996).
Achuthan, et al., "Drug-induced senescence generates chemoresistant stemlike cells with low reactive oxygen species", J. Biol. Chem., 286:37813-29 (2011).
Adjei, "Blocking oncogenic Ras signaling for cancer therapy", J Natl Cancer Inst., 93(14)1062-74 (2001).
Alarcon-Segovia, "Antinuclear antibodies: to penetrate or not to penetrate, that was the question", Lupus, 10:315-8 (2001).
American Cancer Society, Cancer Facts & Figures, pp. 1-70 (2014).
Arnaudeau, et al., "DNA double-strand breaks associated with replication forks are predominantly repaired by homologous recombination involving an exchange mechanism in mammalian cells", J Mol Biol, 307:1235-45 (2001).
ATCC®CCI-86 Raji, "*Homo sapiens* lymphoblast Burkitt\s lymph", http://www.aroc.org/Products/ALL/CCL-86.aspx?&p=1&rel=characteristics, 1 page, retrieved from the Internet Jul. 10, 2015.
ATCC®CRL-1651 COS-7, "Cercopithecus aethiops kidney", http://www.aroc.org/Products/ALL/CRL1651.aspx 1 page, retrieved from the Internet Jul. 12, 2015.
Barka, et al., "Transduction of TAT-HA—galaotosidase Fusion Protein into Salivary Gland-derived Cells and Organ Cultures of the Developing Gland, and into RatSubmandibular Gland In Vivo", Histochem Cytochem., 48(11):1453-60 (2000).
Bassi, et al., "Nuclear PTEN controls DNA repair and sensitivity to genotoxic stress", Science, 341:395-9 (2013).
Bernatsky, et al., Breast, ovarian, and endometrial malignancies in systemic lupus erythematosus: a meta-analysis Br. J. Cancer 104:1478-81(2011a).
Bernatsky, et al., "Cancer risk in systemic lupus: an updated international multi-centre cohort study", J. Autoimmun. 42:130-5 (2013).
Bernatsky, et al., "Decreased breast cancer risk in systemic lupus erythematosus: the search for a genetic basis continues", Lupus, 21:896-9 (2008b).
Bernatsky, et al., "Prostate cancer in systemic lupus erythmatosus", Int. J. Cancer, 129: 2966-9 (2011b).
Bernatsky, et al., "The relationship between cancer and medication exposures in systemic lupus erythaematosus: a case-cohort study", Ann. Rheum. Dis. 67:74-9 (2008).
Bindra, et al., "Down-regulation of Rad51 and decreased homologous recombination in hypoxic cancer cells", Mol. Cell. Biol., 24(19):8504-18 (2004).
Bitzer, et al., "Sendai virus vectors as an emerging negative-strand RNA viral vector system", J Gene Med., 5(7):543-53 (2003).
Broson, et al., "Mutational analysis of avidity and fine specificity of anti-levan antibodies", J Immunol., 163:6694-701 (1999).
Brummel, et al., "Probing the combining site of an anti-carbohydrate antibody by saturation-mutagenesis: role of the heavy-chain CDR3 residues", Biochem., 32(4):1180-7.
Bryant, et al., "Specific killing of BRCA2-deficient tumours woth inhibitors of poly (ADP-ribose) polymerase", Nature, 434:913-7 (2005).
Burks, et al., "In vitro scanning saturation mutagenesis of an antibody binding product", PNAS, 94:412-7 (1997).
Casset, et al., "Peptide mimetic of an anti-CD4 monoclonal antibody by rational design", BBRC, 307:198-205 (2003).
Celldex, "CDX-011 Clinical program", http://www.celldextherapeutics.com/wt/page/cds_011_breast?CMP=KNC-3GS620403736., retrieved from the interned Mar. 31, 2011.
Chan, et al., "Targeting cancer with a cell-penetrating anti-DNA antibody", J Investigative Med., 60(1):148 (2012).
Chen, et al., "Selection and analysis of an optimized anti-VEGF antibody: Crystal structure of an affinity-matured Fab in complex with antigen", J Mol Biol., 283:865-81 (1999).
Chi, et al., "Roles of ATP binding and ATP hydrolysis in human Rad51 recombinase function", DNA Repair (Amst) 5:381-91 (2006).
Chothia and Lest, "Canonical structures for the hypervariable regions of immunoglobulins", J Mol. Biol., 196:901-17 (1987).
Cleaver, et al., "Phosphorylated H2Ax is not an unambiguous marker for DNSA double-strand breaks", Cell Cycle, 10:3223-4 (2011).
Coffin, "HIV population dynamics in vivo: implications for genetic variation, pathogenesis, and therapy", Science, 267:483-9 (1995).
Colburn, et al., "Anti-guanosine antibodies in murine and human lupus have the internal image of G-binding proteins", J Rheumatol., 30(5):993-7 (2003).
Colburn, et al., "Serum antibodies as a marker for SLE disease activity and potential", Clinica Chimica Acta, 370:9-16 (2006).
Coleman, "Effects of amino acid sequence changes on antibody-antigen interactions", Res Immunol., 145:33-6 (1994).
Collingridge, et al., "Pentoxifylline improves the oxygenation and radiarion response of BA 1112 rat rhabdomyosarcomas and EMT6 mouse mammary carcinomas", Int J Cancer, 90(5)1256-64 (2000).
Collins, et al., "Viral vectors in cancer immunotherapy: which vector for which strategy", Curr Gene Ther., 8(2):66-78 (2008).
Cuesta, et al., "Multivalent antibodies: when design surpasses evolution", Trends in Biotechnol., 28(7):355-62 (2010).
Dean, et al, "Current advances in the translation of cascular tissue engineering to the treatment of pediatric congenital heart disease", Yale J Bid Med, 85:229-38 (2012).
DePascalis, et al., "Grafting of abbreviated complementarity-determining regions containing specificity-determining residues essential for ligand contact to engineer a less immurtogenic humanized monoclonal antibody", J Immun., 169:3076-84 (2002).
Derossi, et al,, "The third helix of the Antennapedia homeodomain translocates through biological membranes", J. Biol. Chem. 269(14):10444-50 (1994).
Deyev, et al., "Multivalency: the hallmark of antibodies used for optimization of tumor targeting by design", Bioesseays, 30(9):904-18 (2008).
Dimri, et al., "A biomarker that identifies senescent human cells in culture and in aging skin in vivo", PNAS, 92(20):9363-7 (1995).
Dray, et al., "Molecular basis for enhancement of the meiotic DMC1 recombinase by RAD51 associated protein 1 (RAD51AP1)", PNAS, 108:3560-5 (2011).

(56) References Cited

OTHER PUBLICATIONS

Farmer, et al., "Targeting the DNA repair defect in BRCA mutant cells as a therapeutic strategy", Nature 434:917-21 (2005).
Feng, et al, "Rad52 inactivation is synthetically lethal with BRCA2 deficiency", PNAS, 108:686-91 (2011).
Florica, "The role of topotecan in the treatment of advanced cervical cancer", Gynecol Oncol., 90:S16-21 (2003).
Ford, "Lupus antibody tops cancer cells", Sci Trans Med., 4(157):157-60 (2012).
Foroutan, et al., "Molecular cytogenetic analysis of chemoresistant non-Hodgkin's lymphoma patients with p53 abnormalities using fluorescence in situ hybridisation and comparative genomic hybridisation", Arch Iran Med., 14 (5):321-6 (2011).
Frankel and Pabo, "Cellular uptake of the tat protein from human immunodeficiency virus", Cell, 55(6):1189-93 (1988).
Fusaki, et al., "Efficient induction of transgene-free human pluripotent stem cells using a vector based on Sendai virus, an RNA virus that does not integrate into the host genome", Proc Jpn Acad Ser., 885:348-362 (2009).
Genbank, Accession No. L16981.1, "Mouse lg rearranged L-chain gene, partial cds",1 page, First available May 2, 1995, accessed Mar. 28, 2016.
Genbank, Accession No. AAA65679.1, "immunoglobulin heavy chain, partial [Mus musculus]", 2 pages, First available May 2, 1995, accessed Mar. 28, 2016.
Genbank, Accession No. AAA65681.1, "immunoglobulin light chain, partial [Mus musculus]", 2 pages, First available May 2, 1995, accessed Mar. 28, 2016.
Genbank, Accession No. AAA65682.1, "This CDS feature is included to show the translation of the of the corresponding V_region. Presently translation qualifiers on V_regions features are illegal, partial [Mus musculus", 1 page, First available May 2, 1995, accessed Jun. 21, 2016.
Grudzien-Nogalska, et al., "Phosphorothioate cap analogs stabilize mRNA and increase translational efficiency in mammalian cells", RNA, 13(10):1745-55 (2007).
Gruhne, et al., "Three Epstein-Barr virus latency proteins independently promote genomic instability by inducing DNA damage, inhibiting DNA repair and inactivating cell cycle checkpoints", Oncogene, 28:3997-4008 (2009).
Gu, et al., "Genetic determinants of autoimmune disease abd coronary vasculitis in the MRL-lpr/lpr mouse model of systemic lupus erythematosus", J Immunol., 161:6999-7006 (1998).
Gysin, et al., "Therapeutic strategies for targeting ras proteins", Genes Cancer, 2(3):359-72 (2011).
Hacein-Bey-Abina, et al., "LMO-2associated clonal T cell proliferation in two patients after gene therapy for SCID-X1", Science, 302(5644):415-9 (2003).
Halazonetis, et al., "An oncogene-induced DNA damage model for cancer development", Science, 319(5868):1352-5 (2008).
Hansen, et al. "antibody mediated transduction of therapeutic proteins into living cells", Scientific world, 5(9):782-8 (2005).
Hansen, et al., "Antibody-mediated Hsp70 protein therapy", Brain Res., 1088 (1):187-96 (2006).
Hansen, et al., "Antibody-mediated p53 protein therapy prevents liver metastasis in vivo", Cancer Res., 67(4):1769-74 (2007a).
Hansen, et al., "Intranuclear protein transduction through a nucleoside salvage pathway", J Biol Chem., 282:20790-3 (2007b).
Hansen, et al., "Targeting cancer with a lupus autoantibody", Sci Transl Med., 4:157ra1426 (2012).
Harrington, et al., "VX-680, a ptent and selective small-molecule inhibitor of auroral kinases suppresses tumor growth in vivo", Nat Med., 10:262-7 (2004).
Hayflick, et al., "The limited in vitro lifetime of human diploid cell strains", Exp Cell Res., 37:614-36 (1965).
Ho, et al., "Synthetic protein transduction domains: enhanced transduction potential in vitro and in vivo", Cancer Res., 61(2):474-7 (2001).
Hoeijmakers, "DNA damage, aging, and cancer", N. Engl. J. Med. 361:1475-85 (2009).
Holm, et al., "Functional mapping and single chain construction of the anti-cytokeratin 8 monoclonal antibody TS1", Mol Immun., 44:1075-84 (2007).
Holtkemp, et al., "Modification of antigen-encoding RNA increases stability, translational efficacy, and T-cell stimulatory capacity of dendritic cells", Blood, 108(13):4009-17 (2006).
Hucl, et al., "A syngeneic variance library for functional annotation of human variation: application to BRCA2", Cancer Res., 68:5023-30 (2008).
Itoh, et al., "Diagnostic use of anti-modified nucleoside monoclonal antibody", Tohoku J Exp Med., 168(2):329-31 (1992).
Jain, et al., "Engineering antibodies for clinical applications", Trends in Biotechnol, 25(7):307-16 (2007).
Jang, et al., "Drug delivery and transport to solid tumors", Phar. Res., 20:1337-50 (2003).
Jang, et al., "The structural basis for DNA binding by an anti-DNA autoantibody", Mol Immun.,35:1207-17 (1998).
Jordan, et al., Mechanism of mitotic block and inhibition of cell proliferation by taxol at low concentrations, PNAS, 90:9552-6 (1993).
Kabat, et al., "Sequences of proteins of Immunological Interest", 5 Ed Public Health service, National Institutes of Health, Bethesda Md. (1991).
Kabouridis, "Biological applications of protein transduction technology", Trends in Biotechnol., (11):498-503 (2003).
Kaelin, Jr., et al., "The concept of synthetic lethality in the context of anticancer therapy", Nat Rev Cancer, 5:689-98 (2005).
Kane, et al., "Methylatlon of the hMLH1 promoter correlates with lack of expression of hMLH1 in sporadic colon tumors and mismatch repair-defective human tumor cell lines", Cancer Rev., 57:808-11 (1997).
Kay, "State of the art gene-based therapies: the road ahead", Nature Rev Genetics, 12(5):316-28 (2011).
Kellner, et al., "Boosting ADCC and CDC activity by Fc engineering and evaluation of antibody effector functions", Methods, 65:105-13 (2014).
Kim, et al., "Heavy and light chain variable single domains of an anti-DNA binding antibody hydrolyze both double- and single-stranded DNAs without sequence specificity", J Biological Chem., 281 (22)15287-95 (2006).
Kobayashi, et al., "Tryptophan H33 plays an important role in pyrimidine (6-4) pyrimidone photoproduct binding by a high-affinity antibody", Protein Eng., 12(10):879-84 (1999).
Kozyr, et al., "Anti-DNA autoantibodies reveal toxicity to tumor cell lines", Immunol Lttr., 80:41-7 (2002).
Kumar, et al., "Molecular cloning and expression of the fabs of human autoantibodies in *Escherichia coli*", J Bio Chem., 275:35129-36 (2000).
Lau, et al., "Suppression of HIV-1 infection by a small molecule inhibitor of the ATM kinase", Nat Cell Biol, 7(5): 493-500 (2005).
Lee, et al., "Cell-penetrating autoantibody induces caspase-mediated apoptosis through catalytic hydrolysis of DNA", Bioorg Med Chem., 15:2016-23 (2007).
Lee, et al., "Gene silencing by cell-penetrating, sequence-selective and nucleic-acid hydrolyzing", Nucleic Acid Res., pp. 1-14 (2009).
Levitt, et al., "PTEN-induction in U251 glioma cells decreases the expression of insulin-like growth factor binding protein-2", Biochem Biophys Res Comm., 336:1056-61 (2005).
Lewitzky, et al., "Reprogramming somatic cells towards pluripotency by defined factors", Curr Opin Biotechnol., 18:467-73 (2007).
Li, et al., "Homologous recombination in DNA repair and DNA damage tolerance", Cell Res., 18:99-113 (2008).
Li, et al., "PTEN, a putative protein tyrosine phosphatase gene mutated in human brain, breast, and prostate cancer", Science, 275:1943-7 (1997).
Liao, et al., "The comet assay: a sensitive method for detecting DNA damage in individual cells", Methods, 48(1):46-53 (2009).
Lisi, et al., "Advances in the understanding of the Fc gamma receptors-mediated autoantibodies uptake", Clin Exp Med 11:1-10 (2011).

(56) References Cited

OTHER PUBLICATIONS

Liu, et al., "A novel bivalent single-chain variable fragment (scFV) inhibits the action of tumor necrosis factor [alpha]", Biotechnol App Biochem., 50(4):173-9 (2008).
MacCallam, et al., "Antibody-antigen interactions: Contact analysis and binding site topography", J Mol Biol., 262:732-45 (1998).
Maeda, et al., "Tumor vascular permeability and the EPR effect in macromolecular therapeutics: a review", J Controlled Release, 65:271-84 (2000).
McCabe, et al., "BRCA2-deficient CAPAN-1 cells are extremely sensitive to the inhibition of Poly (ADP-Ribose) polymerase: an issue of potency", Cancer Biology Therapy, 4:934-6 (2005).
McEllin, et al., "PTEN loss compromises homologous recombination repair in astrocytes: implications for glioblastoma therapy with temozolomide or poly(ADP-ribose) polymerase inhibitors", Cancer Res., 70:5457-64 (2010).
Moynahan, et al., "BRCA2 is required for homology-directed repair of chromosomal breaks", Mol Cell, 7:263-72 (2001).
Muller, et al., "TransMabs: cell-penetrating antibodies, the next generation", Exp Opin Biol Ther., 5(2):1-5 (2005).
Nakanishi, et al., "Development of sendai virus vectors and their potential applications in gene therapy and regenerative medicine", Curr Gene Ther., 12(5):410-6 (2012).
Noble, et al., "DNA-damaging autoantibodies and cancer: the lupus butterfly theory", Nature Reviews, 17:429-34 (2016).
Noble, et al., "Optimizing a lupus autoantibody for targeted cancer therapy",, Cancer Res., 75(11):2285-91 (2015).
Noble, et al., "A cell-penetrating nucleoltyic lupus autoantibody damages DNA and is toxic to BRCA2-deficient cancer cells" poster presented at the Proceedings: AACR Annual Meeting 2014; Apr. 5-9, San Diego, CA (2014).
Noble, et al., "A cell-penetrating nucleolytic lupus autoantibody damages DNA and is toxic to BRCA2-deficient cancer cells", Abstract 4220, Cancer Res, 74:4220 (2014).
Okita, et al., "Induction of pluripotency by defined factors", Exp Cell Res., 316(16):2565-70 (2010).
PARP Inhibitor, http://www.parp-inhibitors.com, retrieved from the internet Mar. 31, 2011.
Pavlovic, et al., "Pathogenic and epiphenomenal anti-DNA antibodies in SLE", Autoimmime Diseases, 2010:462841 1-18 (2010).
Porter, et al., "Chimeric antigen receptor-midified T cells in chronic lymphoid leukemia", NEJM, 365(8):725-33 (2011).
Puc, et al., "PTEN loss inhibits CHK1 to cause double stranded-DNA breaks in cells", Cell Cycle, 4:927-9 (2005).
Rabinovich, et al., "Chimeric receptor mRNA transfection as a tool to generate antineoplastic lymphocytes", Human Gene Therapy, 20(1):51-61 (2009).
Rabinovich, et al., "Synthetic messenger RNA as a tool for gene therapy", Hum Gene Ther., 17(10):1027-35 (2006).
Rahman and Isenberg, "Systemic lupus erythematosus", N. Engl. J. Med. 358:929-39 (2008).
Ratnam, et al., "Current development of clinical inhibitors of poly(ADP-ribose) polymerase in oncology", Clin Cancer Res., 13(5):1383-8 (2007).
Ritter, et al., "Gene therapy in transplantation: Toward clinical trials", Curr Opin Mel Ther., 11(5):504-12 (2009).
Rudikoff, et al., "Single amino substitution altering antigen-binding specificity", PNAS, 79:1979-83 (1982).
Sakai, et al., "Functional restoration of BRCA2 protein by secondary BRCA2 mutations in BRCA2-mutated ovarian carcinoma", Cancer Res., 69:6381-6 (2009).
Sancar, et al., "Molecular mechanisms of mammalian NA repair and the DNA damage checkpoints",, Annu Rev Biochem., 73:39-85 (2004).
Scott, et al., "Antibody therapy of cancer", Nature Reviews Cancer, 12:278-87 (2012).
Sliwinska, et al., "Induction of senescence with doxorubicin leads to increased genomic instability of HCT116 cells", Mech. Ageing Dev., 130:24-32 (2009).
Smith-Gill, et al., "Contributions of immunoglobulin heavy and light chains to antibody specificity for lysozyme and two haptens", J Immunol., 139:4135-44 (1987).
Song, et al,, "Light chain of natural antibody plays a dominant role in protein antigen binding", Biochem Biophys Res Comm., 268:390-4 (2000).
Spertini, et al., "Idiotypic vaccination with a murine anti-dsDNA antibody: phase I study in patients with nonactive systemic lupus erythematosus with nephritis", J Rheumatol 269120:2602-8 (1999).
Stachelek, et al., "Potentiation of temozolomide cytotoxicity by inhibition of DNA polymerase beta is accentuated by BRCA2 mutation", Cancer Re.,s 70:409-17 (2010).
Stanulis-Praeger, et al., "Cellular senescence revisited: a review", Mech Ageing Derv, 38:1-48 (1987).
Steck, et al., "Identification of a candidate tumour suppressor gene, MMAC1, at chromosome 10q23.3 that is mutated in multiple advanced cancers", Nat Genet., 15:356-62 (1997).
Stepinski, et al., "Synthesis and properties of mRNA\s containing the novel "anti-reverse" cap analogs 7-methyl(3\-O-methyl)GpppG and 7-methy1 (3\-deoxy)GpppG", RNA 7 (10:1486-95 (2001).
Stone, et al., "Neoadjuvant chemotheraoy and liver transplantation for hepatocellular carcinoma: a pilot study in 20 patients", Gastroenterology, 104(1)196-202 (1993) Abstract Only.
Sung, "Catalysis of ATP-dependent homologous DNA pairing and strand exchange by yeast RAD51 protein", Science 265:1241-3 (1994).
Sung, et al., "DNA strand exchange mediated by a RAD51-ssDNA nucleoprotein filament with polarity opposite to that of RecA", Cell, 82:453-61 (1995).
Sung, et al., "Rad51 recombinase and recombination mediators", J Biol Chem., 278:42729-32 (2003).
te Poele, et al., "DNA damage is able to induce senescence in tumor cells in vitro and in vivo", Cancer Res. 62:1876-1883 (2002).
Tewey, et al., "Adriamycin-induced DNA damage mediated by mammalian DNA topoisomerase II", Science 226:466-8 (1984).
Vajdos, et al., "Comprehensive functional maps of the antigen-binding site of am amti-ErbB2 antibody obtained with shotgun scanning mutagenesis", J Mol Biol., 320:415-28 (2002).
Vlietstra, et al., "Frequent inactivation of PTEN in prostate cancer cell lines and xenografts", Cancer Res., 58:2720-3 (1998).
Wadia and Stan, "Transducible TAT-HA fusogenic peptide enhances escape of TAT-fusion proteins after lipid raft micropinocytosis", Nat Med., 10(3):310-5 (2004).
Walpita, et al., "Reverse genetics of negative-stranded RNA viruses: a global perspective", FEMS Microbiol. Lett., 244(1):9-18 (2005).
Wang, Mutagenesis in mammalian cells induced by triple helix formation and transcription-coupled repair, Science, 271(5250):802-5 (1996).
Ward, et al., "Binding activities of a repertoire of single immunoglobulin variable domains secreted from *Escherichia coli*", Nature, 341:544-6 (1989).
Warren, et al., "Highly efficient reprogramming to pluripotency and directed differentiation of human cells with synthetic modified mRNA", Cell Stem Cell, 7(5):618-30 (2010).
Weisbart, et al., "A cell-penetrating bispecific antibody for therapeutic regulation of intracellular targets", Mol Cancer Ther., 11:2169 (2012).
Weisbart, et al., "A conserved anti-DNA antibody idiotype associated with nephritis in murine and human systemic lupus erythematosus", J Immunol 144(7):2653-8 (1990).
Weisbart, et al., "An autoantibody is modified for use as a delivery system to target the cell nucleus: therapeutic implications", J Autoimmun., 11:539-46 (1998).
Weisbart, et al., "Antibody-mediated transduction of p53 selectively kills cancer cells", Int J Oncol., 25:1867-73 (2004).
Weisbart, et al.,"Construction and expression of a bispecific single-chain antibody that penetrates mutant p53 colon cancer cells and binds p53", Int J Oncology, 25:1113-8 (2004).
Weisbart, et al., "Novel protein transfection of primary rat cortical neurons using an antibody that penetrates living cells", J Immunol., 164: 6020-6 (2000).

(56) References Cited

OTHER PUBLICATIONS

Weisbart, et al.,"Nuclear delivery of p53 C-terminal peptides into cancer cells using scFv fragments of a monoclonal antibody that penetrates living cells", Cancer Lttrs., 195:211-19 (2003).
Wender, et al., "The design, synthesis, and evaluation of molecules that enable or enhance cellular uptake: peptoid molecular transporters", PNAS, 97(24):13003-8 (2000).
Williams, "DNA hydrolysis mechanism and reactivity", Nucleic Acids and Biology vol. 13, pp. 1-7, Marina Zenkova, ED Springer-Verlag Berlin Heidelberg, (2004).
Wu, et al., "Humanization of a murine monoclonal antibody by simultaneous optimization of framework and CDR residues", J Mol Biol., 294:151-62 (1999).
Xu, et al., "Dual DNA unwinding activities of the Rothmund-Thomson syndrome protein, RECQ4", EMBO J 28:568-77 (2009b).
Xu, et al., "MCM10 mediates RECQ4 association with MCM2-7 helicase complex during DNA replication", EMBO J., 28:3005-14 (2009a).
Yee, et al., "The fine specificity of IgG antiguanosine antibodies in systemic lupus erythematosus", Clin Immunol Immunopathol., 36(2):161-7 (1985).
Yoder, et al., "The base excision repair pathway is required for efficient lentivirus integration", PLoS One, 6(3) e17862 (2011).
Yoshizaki, et al., "Naked sendai virus vector lacking all of the envelope-related genes: reduced cytopathogenicity and immunogenicity", J Gene Med., 8(9):1151-9 (2006).
Young, et al. "Abstract 654: targeting K-ras cancer cells with a lupus anti-guanosine antibody", Cancer Res., 74(19 Supp):654 (2014).
Yung, et al., "?Anti-DNA antibodies in the pathogenesis of lupus nephritis—The emerging mechanisms", Autoimmunity Rev., 7(4):317-21 (2008).
Zack, et al., "Novel structural features of aautoantibodies in murine lupis: A possible superantigen binding site", Immonol Cell Biol., 72:513-20 (1994).
Zack, et al., "DNA mimics a self-protein that may be a target for some anti-DNA antibodies in systemic lupus erythematosus", J. Immunol. 154(4):1987-94 (1995).
Zack, et al., "Mechanisms of cellular penetration and nuclear localization of an anti-double strand DNA autoantibody", J Immunol., 157:2082-8 (1996).
Zhan, et al., "Recombinant Fv-Hsp70 protein mediates neuroprotection after focal cerebral ischemia in rats", Stroke, 41(3):538-43 (2010).
International Search Report for corresponding PCT application PCT/US2015/018729 dated Jun. 1, 2015.
U.S. Appl. No. 15/615,416, Hansen.
Ahmed, et al., "Extracellular renal guanosine cyclic 3'5'-monophosphate modulates nitric oxide and pressure-induced natriuresis." Hypertension, 50:958-63 (2007).
Andersen, et al.,"Identification of heme oxygenase-1-specific regulatory CD8+ T cells in cancer patients," Journal of Investigative Medicine (2009).
Apte, et al., "Doxorubicin in TAT peptide-modified multifunctional immunoliposomes demonstrates increased activity against both drug-sensitive and drug-resistant ovarian cancer models" Cancer Biology & Therapy, 15:1, 69-80 (2013).
Chen, et al., "A lupus anti-DNA autoantibody mediates autocatalytic, targeted delivery of nanoparticles to tumors" Oncotarget, 7(37): 59965-59975 (2016).
Colburn, et al., "Circulating antibodies to guanosine in systemic lupus erythematosus: correlation with nephritis and polyserositis by acute and longitudinal analyses." Lupus, 10:410-7 (2001).
Demers, et al., "Cancers predispose neutrophils to release extracellular DNA traps that contribute to cancer-associated thrombosis," Proc Natl Acad Sci USA, 109(32):13076-13081 (2012).
Deutsch, et al., "Guanosine possesses specific modulatory effects on NMDA receptor-mediated neurotransmission in intact mice," Eur Neuropsychopharmacol, 18:299-302 (2008).

Dowdy, et al., "Cationic PTD/CPP-mediated macromolecular delivery: charging into the cell," Expert Opin Drug Deliv, 12:1627-36(2015).
Elbayoumi, et al., "Antinucleosome antibody-modified liposomes and lipid-core micelles for tumor-targeted delivery of therapeutic and diagnostic agents," Journal of Liposome Research, 17:1, 1-14 (2007).
Fujita, et al., "Brain tumor tandem targeting using a combination of monoclonal antibodies attached to biopoly(beta-L-malic acid)," Journal of Controlled Release, 122:3, 356-363 (2007).
Hawes, et al., "Extracellular DNA: A Bridge to Cancer" Cancer Research, 75(20):4260-4264 (2015).
Isenberg, et al., "Fifty years of anti-ds DNA antibodies: are we approaching journey's end?" Rheumatology, 46(7):1052-1056 (2007).
Jackson, et al., "Guanosine regulates adenosine levels in the kidney" Physiol Rep, 2(5). pii: e12028. doi: 10.14814/phy2.12028 (2014).
Kocbek, et al., "Targeting cancer cells using PLGA nanoparticles surface modified with monoclonal antibody" Journal of Controlled Release, 120:1-2, 18-36 (2007).
Liu, et al., "Iniparib Nonselectively Modifies Cysteine-Containing Proteins in Tumor Cells and Is Not a Bona Fide PARP Inhibitor," Clin. Cancer Res. 18:510-523 (2012).
Ma, et al., "Antibodies to guanosine triphosphate misidentified as anti-double-stranded DNA antibodies in a patient with antinuclear antibody-negative lupus, due to buckling of insolubilized assay DNA," Arthritis Rheum, 50:1533-1538 (2004).
Molfetta, et al., "Regulation of fc receptor endocytic trafficking by ubiquitination" Front Immunol, 5:449. Doi: 10.3389/fimmu.2014.00449 (2014).
Noble, et al. "A nucleolytic lupus autoantibody is toxic to BRCA2-deficient cancer cells" Sci Rep, 4:5958, 4 pages (2014).
Rathbone, et al., "Neurotrophic effects of extracellular guanosine" Nucleosides Nucleotides Nucleic Acids, 27:666-72 (2008).
Sano, et al., "DNA isolated from DNA/anti-DNA antibody immune complexes in systemic lupus erythematosus is rich in guanine-cytosine content" J Immunol, 128:1341-1345 (1982).
Sawant, et al., "Nanosized cancer cell-targeted polymeric immunomicelles loaded with superparamagnetic iron oxide particles" Journal of Nanoparticle Research, 11:7, 1777-1785 (2009).
Service, et al., "Nanotechnology. Nanoparticle Trojan homes gallop from the lab into the clinic" Science, 330(6002):314-315 (2010).
Shin, et al., "Pharmacokinetics of guanosine in rats following intravenous or intramuscular administration of a 1:1 mixture of guanosine and acriflavine, a potential antitumor agent" Arch Pharm Res, 31(10):1347-53 (2008).
Shuster, et. al., "DNA hydrolyzing autoantibodies" Science, 1;256(5057):665-7 (1992).
Singh, et al., "A gene expression signature associated with "K-Ras addiction" reveals regulators of EMT and tumor cell survival" Cancer Cell, 15:489-500 (2009).
Stollar, et al., "Nucleoside specificity in the carrier IgG-dependent induction of tolerance" J Immunol, 117:1308-1313 (1976).
Stroun, et al., "About the possible origin and mechanism of circulating DNA apoptosis and active DNA release" Clin Chim Acta, 313(1-2):139-142 (2001).
Sueoka-Aragane, et al., "Correlation between plasma DNA and tumor status in an animal model" PloS One, 9(12) e111881. doi: 10.1371/journal.pone.0111881 (2014).
Swystun, et al., "Breast cancer chemotherapy induces the release of cell-free DNA, a novel procoagulant stimulus" J Thromb Haemost, 9(11):2313-2321 (2011).
Uemura, et al., "Neurochemical analysis of focal ischemia in rats" Stroke, 22:1548-53 (1991).
Weisbart, et al., "Cell type specific targeted intracellular delivery into muscle of a monoclonal antibody that binds myosin IIb" Mol Immunol, 39(13):783-789 (2003).
Weisbart, et al., "DNA-dependent targeting of cell nuclei by a lupus autoantibody" Sci Rep., 5:12022 (2015).
Wen, et al., "Extracellular DNA in pancreatic cancer promotes cell invasion and metastasis" Cancer Research, 73(14):4256-4266 (2013).

(56) References Cited

OTHER PUBLICATIONS

Wu, et al., "pH-sensitive poly(histidine)—PEG/DSPE-PEG copolymer micelles for cytosolic drug delivery" *Biomaterials*, 34:4, 1213-1222 (2013).

Zack, et al., "Two kappa immunoglobulin light chains are secreted by an anti-DNA hybridoma: implications for isotypic exclusion" *Mol Immunol*, 32:1345-53 (1995).

Zhu, et al., "Matrix Metalloprotease 2-Responsive Multifunctional Liposomal Nanocarrier for Enhanced Tumor Targeting" *ACS Nano*, 6:4, 3491-3498 (2012).

* cited by examiner

SEQUENCE LISTING

```
<160> NUMBER OF SEQ ID NOS: 22

<210> SEQ ID NO 1
<211> LENGTH: 107
<212> TYPE: PRT
<213> ORGANISM: Mus musculus

<400> SEQUENCE: 1

Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Ser Ile Ser Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Ile Ser Val Glu Thr
65                  70                  75                  80

Glu Asp Phe Gly Met Tyr Phe Cys Gln Gln Ser Asn Ser Trp Pro Leu
                85                  90                  95
```

Thr Phe Gly Ala Gly Thr Lys Leu Glu Leu Lys
            100                 105

<210> SEQ ID NO 2
<211> LENGTH: 11
<212> TYPE: PRT
<213> ORGANISM: Mus musculus

<400> SEQUENCE: 2

Arg Ala Ser Gln Ser Ile Ser Asn Tyr Leu His
1               5                   10

<210> SEQ ID NO 3
<211> LENGTH: 7
<212> TYPE: PRT
<213> ORGANISM: Mus musculus

<400> SEQUENCE: 3

Tyr Ala Ser Gln Ser Ile Ser
1               5

<210> SEQ ID NO 4
<211> LENGTH: 9
<212> TYPE: PRT
<213> ORGANISM: Mus musculus

<400> SEQUENCE: 4

Gln Gln Ser Asn Ser Trp Pro Leu Thr
1               5

<210> SEQ ID NO 5
<211> LENGTH: 116
<212> TYPE: PRT
<213> ORGANISM: Mus musculus

<400> SEQUENCE: 5

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Ile Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Pro Tyr Thr Met Tyr Tyr Trp Gly Gln Gly Thr Ser Val
            100                 105                 110

Thr Val Ser Ser
        115

<210> SEQ ID NO 6
<211> LENGTH: 5
<212> TYPE: PRT
<213> ORGANISM: Mus musculus

<400> SEQUENCE: 6

Asp Tyr Tyr Met Asn
1               5

<210> SEQ ID NO 7
<211> LENGTH: 17
<212> TYPE: PRT
<213> ORGANISM: Mus musculus

<400> SEQUENCE: 7

Arg Val Asn Pro Ser Asn Gly Gly Ile Ser Tyr Asn Gln Lys Phe Lys
1               5                   10                  15
Gly

<210> SEQ ID NO 8
<211> LENGTH: 7
<212> TYPE: PRT
<213> ORGANISM: Mus musculus

<400> SEQUENCE: 8

Gly Pro Tyr Thr Met Tyr Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Artificial polypeptide linker

<400> SEQUENCE: 9

Gly Gln Ser Ser Arg Ser Ser
1               5

<210> SEQ ID NO 10
<211> LENGTH: 18
<212> TYPE: PRT
<213> ORGANISM: Artificial Sequence
<220> FEATURE:
<223> OTHER INFORMATION: Artifical polypeptide linker

<400> SEQUENCE: 10

Gly Gln Ser Ser Arg Ser Ser Ser Gly Gly Gly Ser Ser Gly Gly Gly
1               5                   10                  15
Gly Ser

<210> SEQ ID NO 11
<211> LENGTH: 6
<212> TYPE: PRT
<213> ORGANISM: Artificial Sequence
<220> FEATURE:
<223> OTHER INFORMATION: Artificial polypeptide linker

<400> SEQUENCE: 11

Gly Ser Gly Ser Gly Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Artifical polypeptide linker

<400> SEQUENCE: 12

Ala Ser Gly Gly Gly Ser
1               5

<210> SEQ ID NO 13
<211> LENGTH: 15
<212> TYPE: PRT
<213> ORGANISM: Artificial Sequence
<220> FEATURE:
<223> OTHER INFORMATION: Artifical polypeptide linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: Artificial polypeptide linker

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 18
<212> TYPE: PRT
<213> ORGANISM: Artificial Sequence
<220> FEATURE:
<223> OTHER INFORMATION: Artificial polypeptide linker

<400> SEQUENCE: 15

Gly Gly Ser Ser Arg Ser Ser Ser Ser Gly Gly Gly Gly Ser Gly Gly
1               5                   10                  15

Gly Gly

<210> SEQ ID NO 16
<211> LENGTH: 11
<212> TYPE: PRT
<213> ORGANISM: Human immunodeficiency virus

<400> SEQUENCE: 16

Tyr Gly Arg Lys Lys Arg Arg Gln Arg Arg
1               5                   10

<210> SEQ ID NO 17
<211> LENGTH: 9
<212> TYPE: PRT
<213> ORGANISM: Human immunodeficiency virus

<400> SEQUENCE: 17

Arg Lys Lys Arg Arg Gln Arg Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Artificial polypeptide sequence

<400> SEQUENCE: 18

Arg Arg Arg Arg Arg Arg Arg
1               5

```
<210> SEQ ID NO 19
<211> LENGTH: 12
<212> TYPE: PRT
<213> ORGANISM: Artificial Sequence
<220> FEATURE:
<223> OTHER INFORMATION: Artificial polypeptide sequence

<400> SEQUENCE: 19

Arg Arg Gln Arg Arg Thr Ser Lys Leu Met Lys Arg
1               5                   10

<210> SEQ ID NO 20
<211> LENGTH: 27
<212> TYPE: PRT
<213> ORGANISM: Artificial Sequence
<220> FEATURE:
<223> OTHER INFORMATION: Artificial polypeptide sequence

<400> SEQUENCE: 20

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 21
<211> LENGTH: 29
<212> TYPE: PRT
<213> ORGANISM: Artificial Sequence
<220> FEATURE:
<223> OTHER INFORMATION: Artificial polypeptide sequence

<400> SEQUENCE: 21

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 22
<211> LENGTH: 16
<212> TYPE: PRT
<213> ORGANISM: Artificial Sequence
<220> FEATURE:
<223> OTHER INFORMATION: Artifiical polypeptide sequence

<400> SEQUENCE: 22

Arg Gln Ile Lys Ile Trp Phe Gln Asn Arg Arg Met Lys Trp Lys Lys
1               5                   10                  15
```

CELL PENETRATING ANTI-GUANOSINE ANTIBODY BASED THERAPY FOR CANCERS WITH RAS MUTATIONS

CROSS-REFERENCE TO RELATED APPLICATIONS

This application is a 371 application of International Application No. PCT/US2015/018729 filed Mar. 4, 2015, which claims benefit of and priority to U.S. Provisional Application No. 61/947,492, filed Mar. 4, 2014.

REFERENCE TO SEQUENCE LISTING

The Sequence Listing submitted Mar. 4, 2015 as a text file named "YU 6265_ST25.txt," created on Mar. 2, 2015, and having a size of 7,000 bytes is hereby incorporated by reference.

FIELD OF THE INVENTION

The invention relates to the field of anti-cancer therapy and in particular to targeted therapy for malignancies associated with mutations in the small GTPase K-Ras.

BACKGROUND OF THE INVENTION

Cancer is the second most common cause of death in the United States, exceeded only by heart disease, accounting for approximately 1 in 4 deaths. In 2015, about 589,430 Americans are expected to die of cancer, almost 1,600 people per day, and there will be an estimated 1,658,370 new cancer cases diagnosed in the U.S. alone. As of Jan. 1, 2014, there were approximately 14.5 million Americans living with cancer, or with a history of cancer (*American Cancer Society*, Cancer Facts & Figures, 2015). The most prevalent cancer types include prostate cancer, breast cancer, lung cancer and colorectal cancer.

The majority of cancer therapies are severely limited by significant side effects due to non-specific tissue toxicity. The identification and development of therapeutic agents that are selectively toxic to malignant cells is a key goal in cancer research. Many tumors harbor genetic defects that distinguish them from normal cells, and some of these defects have the potential to be exploited in the development of targeted therapies for cancer.

A significant amount of work has focused on applying the specific binding activity of monoclonal antibodies to the development of tumor-specific therapies. Select antibodies such as trastuzumab (HERCEPTIN®), rituximab (RITUXAN®), and cetuximab (ERBITUX®) have received approval for use in human cancer therapy. However, all of these therapeutic antibodies lack the ability to penetrate into cancer cells and are therefore limited to attacking targets located on the external surface of tumor cells, such as growth factors and membrane receptors.

Approximately 30% of all human malignancies are associated with mutations in the Ras family of small GTPase proteins. Amongst the Ras family of GTPases, mutation in the K-Ras gene is most frequently associated with development of cancer. Cells with activating K-Ras mutations are highly associated with specific tumor types, including pancreatic, colorectal, and lung cancers. However, the cell membrane is substantially impermeable to many larger macromolecules, and the intracellular Ras molecule has long been considered an un-drugable target due to its location.

Current approaches to the therapeutic regulation of intracellular targets are largely based on the use of small molecules that are capable of passive diffusion into cells. However, small-molecule inhibitors are prone to causing off-target effects that can result in significant toxicity, and at present there are no highly effective methods of specifically targeting cancer cells harboring mutant K-Ras.

It is therefore an object of the invention to provide agents and methods of use thereof that selectively target cells with aberrant G-protein signaling, particularly those cells that rely on such signaling for proliferation and survival.

It is a further object of the invention to provide agents and methods of use thereof that are selectively cytotoxic to cancer cells and other undesirable cells that possess mutations in the small GTPase K-Ras.

SUMMARY OF THE INVENTION

Cell-penetrating autoantibodies capable of binding to guanosine (anti-guanosine Abs) are provided. The antibodies are typically more toxic to cells harboring mutant small GTPase K-Ras genes than cells with wild-type K-Ras. The examples below illustrate that an exemplary cell-penetrating anti-guanosine mAb, referred to herein as 4H2, is more toxic to cells harboring a range of mutations in the small GTPase K-Ras than to their counterpart cells that have wild-type K-Ras. It is believed that cell-penetrating anti-guanosine mAbs specifically target cancer cells with activating K-Ras mutations.

Pharmaceutical compositions including one or more cell-penetrating anti-guanosine antibodies or antigen binding fragments or fusions or variants thereof in an amount effective to prevent, reduce or inhibit the growth or proliferation of cells having one or more amino acid mutations in the small GTPase K-Ras are disclosed. Cell-penetrating anti-guanosine antibodies antibody or antigen binding fragment or fusion thereof can be effective to inhibit or reduce phosphorylation of ERK and/or Akt in a cell as compared to an untreated control cell. In some embodiments, the cell-penetrating anti-guanosine antibody or antigen binding fragment or fusion or variant thereof is present in an amount that is effective to cause cytotoxicity to cells harboring mutant K-Ras. Typically, the pharmaceutical compositions include one or more cell-penetrating anti-guanosine antibodies or antigen binding fragments or fusions or variants thereof in an amount from about 0.01 mg/kg to about 100 mg/kg body weight of a human. The pharmaceutical composition can be in a unit dosage form, for example, suitable for intravenous injection or intra-tumoral injection.

An exemplary cell-penetrating anti-guanosine antibody is monoclonal antibody 4H2, or a variant or fragment thereof that binds the same epitope(s) as 4H2. In preferred embodiments, the anti-guanosine antibody is a humanized variant or antigen binding fragment or fusion a variant of monoclonal antibody 4H2. Preferred antigen binding fragments include single chain variable fragments (scFv) of anti-guanosine antibodies, or conservative variants thereof. For example, the anti-guanosine antibody can be a single chain variable fragment of 4H2 (4H2 scFv), or conservative variant thereof. The 4H2 scFv is preferably produced as an antibody fragment including the framework regions of a human antibody. In certain embodiments the scFv is produced as a recombinant protein expressed from an expression vector in a mammalian cell, or yeast cell such as *Pichia pastoris*.

In preferred embodiments, the scFv includes a heavy chain variable domain and a light chain variable domain. In some embodiments, the light chain variable domain includes the amino acid sequence of SEQ ID NO: 1, or includes one, two, or three CDRs having the amino acid sequence of SEQ ID NO: 2, SEQ ID NO: 3 or SEQ ID NO: 4, or a combination thereof. The heavy chain variable domain can include the amino acid sequence of SEQ ID NO: 5, or includes one, two, or three CDRs having the amino acid sequence of SEQ ID NO: 6, SEQ ID NO: 7 or SEQ ID NO: 8, or a combination thereof. In preferred embodiments, the scFv includes six CDRs having the amino acid sequence of SEQ ID NOS: 2, 3, 4, 6, 7 and 8.

The pharmaceutical compositions can include one or more additional therapeutically active agents. Exemplary additional therapeutically active agents include antineoplastic or radio-sensitizing agents selected from the group including cisplatin, cytoxan, doxorubicin, methotrexate, mitomycin c, nitrogen mustard, hydroxyurea, bevacizumab, cetuximab, rituximab, and trastuzumab tirapazamine, temozolomide, camptothecin, cisplatin, gemcitabine, 5-fluorouracil, hydroxyurea, pentoxifylline, and vinorelbine, or a combination thereof. The pharmaceutical compositions can be formulated for intravenous injection, intratumoral injection or oral administration.

Methods of treating or preventing cancer including administering to a subject in need thereof a pharmaceutical composition including one or more cell-penetrating anti-guanosine antibodies or antigen binding fragments or fusions or variants thereof in an amount effective to cause cytotoxicity to cells harboring mutant K-Ras are provided. Preferably the antibodies or fragments thereof have little, no, or at least relatively less toxicity to non-cancerous cells compared to cancer cells or other cells containing a mutant K-Ras. Typically, the methods include an amount of the one or more cell-penetrating anti-guanosine antibodies or fragments thereof effective to prevent, inhibit or reduce one or more symptoms of cancer. Exemplary cancers that can be treated include breast cancers, colon cancers, endometrial tumors, brain tumors, ovarian, and pancreatic cancers, leukemias and other cancers of the blood and lymphatic system, cancers of the genitourinary system, cancers of the nervous system, cancers of the head and neck, lung cancers, gynecologic cancers, gastrointestinal cancers, skin cancers, and pediatric cancers.

The methods can be useful for treating cancer that is resistant to radiotherapy or resistant to chemotherapy. Typically, the methods are useful for treating cancer that is characterized by activating K-Ras mutations.

In some embodiments the subject is at risk of developing cancer. The subject can be diagnosed with one or more mutations in the K-Ras gene. The mutations can be at a position that causes aberrant activation of K-Ras proteins, including but not limited to mutations in codons 12, 13, and 61 that result in changes in amino acids at positions mutations at 12, 13, and/or 61 in the K-Ras protein. In a particular embodiment the activating mutation in K-Ras is a mutation at position 12 selected from the group including G12S, G12C, G12T, G12D and G12A.

The methods can also include treating the subject with radiation therapy, wherein the cell-penetrating anti-guanosine antibody increases the cell's sensitivity to radiation therapy. Preferably, the methods increase the cell's sensitivity to radiation therapy by at least 10%. The cell-penetrating anti-guanosine antibody can be administered to the subject at least 24 hours before the radiation therapy, concurrently with radiation therapy, or within 24 hours after radiation therapy.

The methods can also include treating the subject with chemotherapy, wherein the cell-penetrating anti-guanosine antibody increases the cell's sensitivity to the chemotherapy. Preferably, the methods increase the cell's sensitivity to chemotherapy by at least 10%. The cell-penetrating anti-guanosine antibody can be administered to the subject at least 24 hours before the chemotherapy, concurrently with chemotherapy, or within 24 hours after chemotherapy.

In some embodiments, the cell-penetrating anti-guanosine antibodies are derived from the serum of a patient with an autoimmune disease or from the serum of an animal model of an autoimmune disease. In preferred embodiments the cell-penetrating anti-guanosine antibody is transported into the cytoplasm of the cell without the aid of a carrier or conjugate.

Methods of reducing the number of viable cells having a mutation in one or more of the small GTPase Ras genes in a subject, including administering to the subject an effective amount of a composition including one or more cell-penetrating anti-guanosine antibodies or antigen binding fragments or fusions thereof to reduce the phosphorylation of ERK and/or Akt in a cell as compared to an untreated control cell are also provided.

DETAILED DESCRIPTION OF THE INVENTION

I. Definitions

Figure 1:
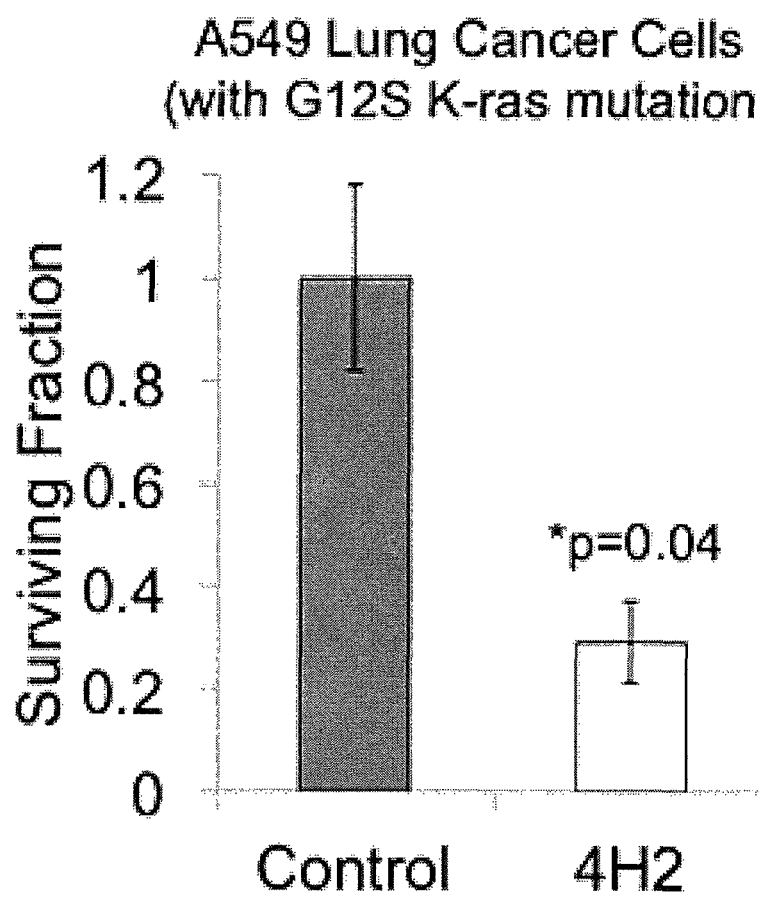
FIG. 1 is a bar graph showing the surviving fraction of A549 lung cancer cells with G12S mutation in K-Ras in the presence of buffer only (control) or mAb 4H2 (1.5 mg/mL), respectively. Error bars reflect standard error of the mean (SEM).

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

As used herein, the term "4H2" refers to a monoclonal antibody including the amino acid sequence set forth in SEQ ID NO: 1.

As used herein, the term "scFv" as used herein means a single chain variable fragment that includes a light chain variable region (VL) and a heavy chain variable region (VH) joined by a linker. The VL and VH regions may be derived from the parent antibody or may be chemically or recombinantly synthesized.

As used herein, the term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (CDR L1), 50-56 (CDR L2) and 89-97 (CDR L3) in the light chain variable domain and at approximately residues 27-35

(CDR H1), 50-65 (CDR H2) and 95-102 (CDR H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (CDR L1), 50-52 (CDR L2) and 91-96 (CDR L3) in the light chain variable domain and 26-32 (CDR H1), 53-55 (CDR H2) and 96-101 (CDR H3) in the heavy chain variable domain; Chothia and Lesk, 1987, *J. Mol. Biol.* 196:901-917).

As used herein, the term "Framework Region" or "FR" residues are those variable domain residues other than the hypervariable region residues as herein defined.

The term "polypeptide" refers to a chain of amino acids of any length, regardless of modification (e.g., phosphorylation or glycosylation). In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Tip, W), Tyrosine (Tyr, Y), and Valine (Val, V).

As used herein, a "variant," "mutant," or "mutated" polynucleotide contains at least one polynucleotide sequence alteration as compared to the polynucleotide sequence of the corresponding wild-type or parent polynucleotide. Mutations may be natural, deliberate, or accidental. Mutations include substitutions, deletions, and insertions.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or includes a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "cell-penetrating antibody" refers to an immunoglobulin protein, fragment, or variant thereof that is transported across the cell membrane (i.e., into the cytoplasm) of living mammalian cells. The antibody can be transported into the cytoplasm of the cells without the aid of a carrier or conjugate. In some embodiments, the antibody, fragment, or variant thereof is conjugated to a cell-penetrating moiety, such as a cell penetrating peptide.

The term "anti-guanosine antibody" refers to an immunoglobulin protein, fragment, or variant thereof that specifically binds to the purine nucleoside guanosine. Anti-guanosine antibodies can also recognize modified or phosphorylated forms of guanosine, including guanosine monophosphate (GMP), cyclic guanosine monophosphate (cGMP), guanosine diphosphate (GDP), and guanosine triphosphate (GTP). Anti-guanosine antibodies can bind to guanosine within single or double stranded DNA or RNA, including ribosomal RNA, messenger RNA and transfer RNA.

The term "specifically binds" refers to the binding of an antibody to its cognate antigen (e.g., single-stranded and/or double-stranded DNA) while not significantly binding to other antigens. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with that second molecule.

The term "monoclonal antibody" or "mAb" refers to an antibody obtained from a substantially homogeneous population of antibodies, i.e., the individual antibodies within the population are identical except for possible naturally occurring mutations that may be present in a small subset of the antibody molecules.

The term "G-Protein" refers to guanine nucleotide-binding proteins that bind to and hydrolyze guanosine triphosphate (GTP) to guanosine diphosphate (GDP).

The term "Ras" refers to the family of cytosolic small GTPase enzymes that hydrolyze guanosine triphosphate (GTP) to form guanosine diphosphate (GDP). Ras proteins are activators of several intracellular signaling pathways which ultimately regulate cell growth, differentiation and survival. Mutations in Ras genes that lead to aberrant or constitutive activation of Ras proteins can lead to abnormal cell proliferation and have been associated with cancer.

The term "extracellular-regulated kinase" or "ERK" refers to any of the widely expressed protein kinase intracellular signaling molecules that are involved in biological functions including the regulation of meiosis, mitosis, and post-mitotic functions in differentiated cells. Phosphorylation of ERKs leads to the activation of their kinase activity followed by the step-wise addition of phosphate groups from one intra cellular molecule to another within the cytoplasm of the cell. ERK proteins include the mammalian mitogen-activated protein kinase (MAPK) family, ERK1, ERK2, MAPK1, MAPK2, MEK, etc.

The term "Akt" or "Protein kinase B" (PKB), refers to any serine/threonine-specific protein kinase that is activated by phosphorylation and plays a key role in cellular survival processes such as glucose metabolism, apoptosis, cell proliferation, transcription and cell migration. Phosphorylation of Akt is associated with the survival, proliferation, and invasiveness of malignant cells.

The term "neoplasm" or "neoplastic" refers to cells undergoing abnormal cell proliferation.

The term "therapeutically effective" means that the amount of the composition used is of sufficient quantity to ameliorate one or more causes or symptoms of a disease or disorder. Such amelioration only requires a reduction or alteration, not necessarily elimination. A therapeutically effective amount of a composition for treating cancer is preferably an amount sufficient to cause tumor regression or to sensitize a tumor to radiation or chemotherapy.

The term "pharmaceutically acceptable carrier" encompasses any of the standard pharmaceutical carriers, such as a phosphate buffered saline solution, water and emulsions such as an oil/water or water/oil emulsion, and various types of wetting agents. The carrier is selected to minimize any degradation of the active ingredient and to minimize any adverse side effects in the subject, as would be well known to one of skill in the art.

The term "treatment" refers to the medical management of a patient with the intent to cure, ameliorate, stabilize, or prevent one or more symptoms of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" means to decrease one or more of an activity, symptom, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

II. Compositions

A. Anti-Cancer Antibodies

Compositions for selectively targeting malignancies associated with K-Ras are disclosed. Antibodies are attractive candidates for application in targeted cancer therapy due to their binding specificity. It has been established that antibodies which recognize guanosine moieties can effectively target cancer cells that have mutations in the small GTPase K-Ras (i.e., malignancies associated with K-Ras). Effective delivery of therapeutic agents to within the cytoplasm of the cell nuclei is challenging (Hoeijmakers, *N. Engl. J. Med.* 361:1475-1485 (2009)), but a subset of antibodies which can penetrate into the cytoplasm of live cells has been identified and provides a means for this selective methodology to treat this class of cancers.

1. Cell Penetrating Anti-Guanosine Antibodies

Antibodies that specifically enter into the cell to bind to guanosine, and antigen binding fragments and fusions can be used to penetrate the cell and selectively kill cells that have mutant Ras genes. In some embodiments, the antibodies directly localize to cytoplasm of living cells and bind to guanosine. These antibodies can prevent, reduce or inhibit G-protein signaling and selectively kill malignant cells that exhibit aberrant G-protein signaling due to mutations in genes encoding small GTPases such as the Ras family of proteins.

The cell-penetrating antibodies can penetrate the cell membrane to enter the cytoplasmic space of a wide variety of different cell types, irrespective of the tissue type or location of the cell within the body. For example, the cell-penetrating antibodies can penetrate into cancer cells regardless of the tissue type or location of the cancer. Cell-penetration by anti-guanosine antibodies can be Fc-specific, or can occur independently of the Fc region. For example, where internalization is independent of the Fc region, cellular uptake can involve clathrin-dependent or clathrin independent endocytosis or pinocytosis or lipid raft formation or nucleoside transporter dependent mechanisms.

Following cellular uptake across the cell membrane, cell-penetrating antibodies can be localized to any major intracellular organelles, including mitochondria, ribosomes, endoplasmic reticulum, and lysosomes. In certain embodiments the cell-penetrating antibodies do not localize to the cell nucleus. In preferred embodiments, the cell-penetrating antibodies localize to the mitochondria. In addition, cell-penetrating antibodies may localize to the cytosol. In addition, cell-penetrating antibodies may interact directly with Ras and its variants.

Cell penetrating anti-cancer antibodies can be specific for purine nucleosides containing guanine attached to a ribose (ribofuranose) ring via a β-N9-glycosidic bond. The antibodies can bind guanosine moieties including guanosine triphosphate (GTP) and guanosine diphosphate (GDP). The antibodies can recognize any epitope present on a guanosine moiety (see Formula I). For example, the antibodies can bind across the carbon atoms at the No. 1 and No. 7 positions of the Formula I. Typically, the epitope will include oxygen bound to the No. 6 position of Formula I (Colburn, et al., J Rheumatol., 30 (5), pp. 993-997 (2003)). The antibodies can bind to Ras when it is bound to guanosine moieties.

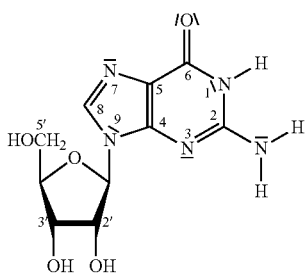

Formula 1

Guanosine with numbered carbon atoms

Typically, the cell penetrating anti-guanosine antibodies recognize and bind to guanosine and inhibit, reduce or prevent G-protein signaling. The recognition and binding can occur within the cytoplasm of the cell. Typically, the interaction between the antibody and guanosine occurs in an intracellular location that is distinct from the cell nucleus. Preferably, the antibodies specifically bind to target nucleosides with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more).

Cell penetrating anti-guanosine antibodies or fragments thereof that target and bind guanosine give rise to significant cytotoxicity amongst cancer cells harboring a range of mutations in the small GTPase K-Ras. In preferred embodiments, the antibodies or fragments thereof are transported into the cytoplasm of the cells without the aid of a carrier or conjugate.

In other embodiments, the antibodies or fragments thereof can be conjugated to a cell-penetrating moiety, such as a cell penetrating peptide to facilitate entry into the cell and transport to the nucleus. Examples of cell penetrating peptides include, but are not limited to, Polyarginine (e.g., R$_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). In other embodiments, the antibody is modified using TRANSMABS™ technology (InNexus Biotech., Inc., Vancouver, BC).

In some embodiments, the antibody or fragment thereof is modified using TransMabs™ technology (InNexus Biotech., Inc., Vancouver, BC). In preferred embodiments, the cell-penetrating anti-guanosine antibodies are lethal to cells with mutant K-Ras.

Antibodies that can be used include whole immunoglobulin (i.e., an intact antibody) of any class, fragments thereof, and synthetic proteins containing at least the antigen binding variable domain of an anti-guanosine antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the antibodies contain at least the components of the CDRs necessary to penetrate cells, maintain guanosine binding and/or interfere with G-protein signaling. In preferred embodiments, the variable region of the disclosed anti-guanosine antibodies contains all three properties.

In a preferred embodiment the cell-penetrating anti-guano sine antibodies is the IgG$_{2a}$ monoclonal anti-DNA antibody 4H2, or a variant or fragment thereof that binds the same epitope(s) as 4H2 (Weisbart, et al., J Immunol., 144, p. 2653-8 (1990); Colburn, et al., Clin Chim Acta 370(1-2): 9-16 (2006); Colburn et al., J Rheumatol 30(5): 993-7 (2003); and Hansen, et al., Sci Transl Med, 4(157): 157ra142 (2012)). mAb 4H2 is a lupus autoantibody that was tested for its effects on a matched pair of cancer cells having wild-type and mutant K-Ras genes, respectively. mAb 4H2 selectively suppressed growth of cancer cells having mutant K-Ras, but had little effect on the cancer cells with wild-type K-Ras (see Examples and FIGS. 1 and 2).

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the carboxyl (COOH)-terminus of one variable domain is tethered to the amino ($NH_2$)-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

2. Sources of Cell Penetrating Anti-Guanosine Antibodies

Cell penetrating anti-guanosine anti-cancer antibodies can be autoantibodies, such as those produced in the course of the auto-immune disease systemic lupus erythematosus (SLE). SLE is an autoimmune disease in which inappropriate production of autoantibodies results in widespread inflammation, tissue damage and organ dysfunction (Rahman and Isenberg, *N. Engl. J. Med.* 358:929-939 (2008)). SLE is associated with an overall increased risk of malignancy but lower than expected rates of tumors associated with defects in BRCA2 such as breast, ovarian, and prostate cancers (Bernatsky, et al., *Br. J. Cancer* 104:1478-1481 (2011); Bernatsky, et al., *Int. J. Cancer,* 129, 2966-2969 (2011); Bernatsky, et al., *J. Autoimmun.* 42:130-135(2013). The pathophysiology underlying this risk profile is unknown and is likely multifactorial (Bernatsky, et al., *Lupus,* 21:896-899 (2008); Bernatsky, et al., *Ann. Rheum. Dis.* 67:74-79 (2008)). A subset of lupus autoantibodies is capable of cellular penetration, as described in PCT/US2012/31860.

Autoantibodies to guanosine are frequently identified in the serum of patients with SLE and are often implicated in disease pathogenesis (Yee, et al., Clin Immunol Immunopathol. 36(2):161-7 (1985)).

In some embodiments, anti-guanosine antibodies derived or isolated from patients with SLE can suppress growth of cells harboring gain-of-function Ras mutations, such as cancer cells.

Useful cell-penetrating anti-guanosine antibodiescan be isolated from lymphocytes isolated from a human subject or a mouse or other experimental animal with an autoimmune disease, such as SLE. For example, monoclonal anti-guanosine antibody 4H2 can be isolated from the MRL/MpJ-Fas$^{lpr}$ lupus mouse model. MRL/MpJ-Fas$^{lpr}$ mice are commercially available from multiple sources (for example, JAX® Mice, Clinical & Research Services; Stock Nos. 000485 and 006825). Isolation of antibodies can be achieved by making a hybridoma from lymphocytes isolated from a human subject or a MRL/MpJ-Fas$^{lpr}$ mouse or other experimental animal. Suitable antibodies include full-length antibodies, single chain antibodies, and antibody fragments.

Cell penetrating anti-guanosine antibodies can also be produced by recombinant, means, for example as a recombinant protein expressed from an expression vector in a mammalian cell, bacterial cell or yeast cell. In preferred embodiments, recombinant antibodies have the same epitope specificity as monoclonal antibody 4H2, produced by MRL/MpJ-Fas$^{lpr}$ mice. This can be achieved by producing a recombinant antibody that contains the paratope of monoclonal antibody 4H2.

3. Modifications of Cell Penetrating Anti-Guanosine Antibodies

Cell penetrating anti-guanosine antibodies and antigen binding fragments and fusions thereof can be modified to improve their therapeutic potential. For example, in some embodiments, the antibody is conjugated to another antibody specific for a second therapeutic target within the cancer cell. For example, the cell-penetrating anti-guanosine antibody can be a fusion protein containing 4H2 Fv and a single chain variable fragment of a monoclonal antibody that specifically binds the second therapeutic target. In other embodiments, the cell-penetrating anti-guanosine antibody is a bi-specific antibody having a first heavy chain and a first light chain from 4H2 and a second heavy chain and a second light chain from a monoclonal antibody that specifically binds the second therapeutic target.

i. Single Chain Variable Fragments

The single chain variable fragments disclosed herein typically include antigen binding fragments of 3E10, or a variant thereof. The monoclonal antibody 3E10 and active fragments and exemplary variants thereof that are transported in vivo to the nucleus of mammalian cells without cytotoxic effect are discussed in U.S. Pat. Nos. 4,812,397 and 7,189,396, and U.S. Published Application No. 2014/0050723.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hyper-variable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

The fragments and fusions of antibodies disclosed herein have bioactivity. The fragments and fusions, whether attached to other sequences or not, can include insertions, deletions, substitutions, or other selected modifications of particular regions or specific amino acids residues, provided the activity of the fragment or fusion is not significantly reduced or impaired compared to the non-modified antibody or antibody fragment.

Light Chain Variable Region

An amino acid sequence for the kappa light chain variable region (VL) of 4H2 is:
D I V L T Q S P A T L S V T P G D R V S L S C <u>RASQSISNYLH</u> W Y Q Q K S H E S P R L L I K <u>YASQSIS</u> G I P S R F S G S G S G T D F T L S I I S V E T E D F G M Y F C <u>QQSNSWPLT</u> F G A G T K L E L K (SEQ ID NO: 1). The complementarity determining regions (CDRs) are shown with underlining, including CDR L1: R A S Q S I S N Y L H (SEQ ID NO: 2); CDR L2: Y A S Q S I S (SEQ ID NO: 3); CDR L3: Q Q S N S W P L T (SEQ ID NO: 4).

Heavy Chain Variable Region

An amino acid sequence for the heavy chain variable region (VH) of 4H2 is:
S E V Q L Q Q S G P E L V K P G A S V K M S C K A S G Y T F T <u>DYYMN</u> W V K Q S H G K S L E W I G <u>RVNPSNGGISYNQKFKG</u> K A T L T V D K S L S T A Y M Q L N S L T S E D S A V Y Y C A R <u>G P Y T M Y Y</u> W G Q G T S V T V S S (SEQ ID NO: 5). The complementarity determining regions (CDRs) are shown with underlining, including CDR H1: D Y Y M N (SEQ ID NO: 6); CDR H2: R V N P S N G G I S Y N Q K F K G (SEQ ID NO: 7); CDR L3: G P Y T M Y Y (SEQ ID NO: 8).

ii. Linkers

The term "linker" as used herein includes, without limitation, peptide linkers. The peptide linker can be any size provided it does not interfere with the binding of the epitope by the variable regions. In some embodiments, the linker includes one or more glycine and/or serine amino acid residues. Monovalent single-chain antibody variable fragments (scFvs) are fragments in which the C-terminus of one variable domain is typically tethered to the N-terminus of the other variable domain via a 15 to 25 amino acid peptide or linker. The linker is chosen to permit the heavy chain and light chain to bind together in their proper conformational orientation. Linkers in diabodies, triabodies, etc., typically include a shorter linker than that of a monovalent scFv as discussed above. Di-, tri-, and other multivalent scFvs typically include three or more linkers. The linkers can be the same, or different, in length and/or amino acid composition. Therefore, the number of linkers, composition of the linker(s), and length of the linker(s) can be determined based on the desired valency of the scFv as is known in the art. Preferably the linker(s) allows for or drives formation of a di-, tri-, and other multivalent scFv.

For example, a linker can include 4-8 amino acids. In a particular embodiment, a linker includes the amino acid sequence GQSSRSS (SEQ ID NO: 9). In another embodiment, a linker includes 15-20 amino acids, preferably 18 amino acids. In a particular embodiment, the linker includes the amino acid sequence GQSSRSSSGGGSSGGGS (SEQ ID NO:10). Other flexible linkers include, but are not limited to, the amino acid sequences Gly-Ser, Gly-Ser-Gly-Ser (SEQ ID NO:11), Ala-Ser, Gly-Gly-Gly-Ser (SEQ ID NO:12), $(Gly_4-Ser)_3$ (SEQ ID NO:13) and $(Gly_4-Ser)_4$ (SEQ ID NO:14), and GGSSRSSSSGGGGSGGGG (SEQ ID NO:15).

iii. Multivalent ScFvs

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. These antibodies are known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They can exhibit an even higher affinity to their targets than diabodies iv. Variants The scFv can be composed of an antibody fragment or fusion protein including an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of 4H2 (e.g., SEQ ID NO: 1 or 5), and which binds to the epitope of 4H2, is selectively lethal to cancer cells or other cells having mutant K-Ras, or selectively increases the radiosensitivity and/or chemosensitivity of cells having mutant K-Ras, or a combination thereof. The scFv can be composed of an antibody fragment or fusion protein that includes a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the variable heavy chain and/or light chain of 4H2 (e.g., SEQ ID NO: 2 or 3 or 4; and/or 6, or 7, or 8), and which binds to the epitope of 4H2, is selectively lethal to cancer cells or other cells having mutant K-Ras, or selectively increases the radiosensitivity and/or chemosensitivity of cells having mutant K-Ras, or a combination thereof. The determination of percent identity of two amino acid sequences can be determined by BLAST protein comparison. In preferred embodiments, scFv includes one, two, three, four, five, or more preferably, all six of the CDRs of the above-described preferred variable domains and which binds to the epitope of 4H2, is selectively lethal to cancer cells or other cells having mutant K-Ras, or selectively increases the radiosensitivity and/or chemosensitivity of cells having mutant K-Ras, or a combination thereof.

In some embodiments, antibody fragment or fusion protein is modified to alter its half-life. In some embodiments, it is desirable to increase the half-life of the antibody fragment or fusion protein so that it is present in the circulation or at the site of treatment for longer periods of time. For example, where the antibody fragments or fusion proteins are being used alone to treat cancer, e.g., cancer cells having impaired DNA repair, it may be desirable to maintain titers of the antibody fragment or fusion protein in the circulation or in the location to be treated for extended periods of time. In other embodiments, the half-life of the antibody fragment or fusion protein is decreased to reduce potential side effects. For example, where the antibody fragment or fusion protein is being used in conjunction with radiotherapy or chemotherapy, the antibody fragment or fusion protein is preferably present in the circulation at high doses during the treatment with radiation or antineoplastic drug but is otherwise quickly removed from the circulation. Antibody fragments, such as 4H2 scFv, are expected to have a shorter half-life than full size antibodies. Other methods of altering half-life are known and can be used in the described methods. For example, antibody fragments and fusion proteins can be engineered with Fc variants that extend half-life, e.g., using XTEND™ antibody half-life prolongation technology (Xencor, Monrovia, Calif.).

v. Humanized Sequences

Many non-human antibodies (e.g., those derived from mice, rats, or rabbits) are naturally antigenic in humans, and thus can give rise to undesirable immune responses when administered to humans. Therefore, humanized 4H2 antibodies, antibody fragments and fusions are provided. The humanized antigen binding molecules may lessen the chance that the antibodies or antibody fragments or scFv will evoke an undesirable immune response when administered to a human.

Humanized forms of non-human (e.g., murine) antibodies include chimeric immunoglobulins, immunoglobulin chains or fragments thereof which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody can optimally contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies are preferably prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

4. Additional Domains and Moieties

The antibodies, antigen binding fragments, and fusion proteins disclosed herein can optionally include one or more additional domains, targeting moieties, and/or tags, etc.

In some embodiments the therapeutic function of the antibody is enhanced by coupling the antibody or a fragment thereof with an additional therapeutic agent. Such coupling of the antibody or fragment with the additional therapeutic agent can be achieved by making an immune-conjugate or by making a fusion protein, or by linking the antibody or fragment to a nucleic acid such as siRNA, including the antibody or antibody fragment and the therapeutic agent.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. The DNA sequence will then be expressed by a cell as a single protein. The protein can be engineered to include the full sequence of both original proteins, or only a portion of either. If the two entities are proteins, often linker (or "spacer") peptides are also added which make it more likely that the proteins fold independently and behave as expected.

i. Protein Transduction Domains

In some embodiments, the antigen binding molecule includes one or more domains for enhancing delivery of the polypeptide across the plasma membrane into the interior of cells. For example, antibody fragments and fusion proteins can be modified to include a protein transduction domain (PTD), also known as a cell penetrating peptide (CPPS). PTDs are known in the art, and include, but are not limited to, small regions of proteins that are able to cross a cell membrane in a receptor-independent mechanism (Kabouridis, P., *Trends in Biotechnology* (11):498-503 (2003)). Although several of PTDs have been documented, the two most commonly employed PTDs are derived from TAT (Frankel and Pabo, *Cell*, 55(6):1189-93(1988)) protein of HIV and Antennapedia transcription factor from *Drosophila*, whose PTD is known as Penetratin (Derossi et al., *J Biol. Chem.*, 269(14):10444-50 (1994)).

The Antennapedia homeodomain is 68 amino acid residues long and contains four alpha helices. Penetratin is an active domain of this protein which includes a 16 amino acid sequence derived from the third helix of Antennapedia. TAT protein includes 86 amino acids and is involved in the replication of HIV-1. The TAT PTD includes an 11 amino acid sequence domain (residues 47 to 57; YGRKKRRQRRR (SEQ ID NO:16)) of the parent protein that appears to be critical for uptake. Additionally, the basic domain TAT (49-57) or RKKRRQRRR (SEQ ID NO:17) has been shown to be a PTD. TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc. Natl. Acad. Sci. USA.*, 97(24):13003-8 (2000)) to up to 33 fold in mammalian cells. (Ho et al., *Cancer Res.*, 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include, but are not limited to, poly-Arg-RRRRRRR (SEQ ID NO:18); PTD-5-RRQRRTSKLMKR (SEQ ID NO:19); Transportan GWTLNSAGYLLGKINLKALAALAKKIL (SEQ ID NO:20);

KALA-WEAKLAKALAKALAKHLAKALAKALKCEA (SEQ ID NO:21); and RQIKIWFQNRRMKWKK (SEQ ID NO:22).

In some embodiments, the fusion protein includes an endosomal escape sequence that improves delivery of the protein to the interior of the cell. Endosomal escape sequences are known in the art, see for example, Barka, et al., *Histochem. Cytochem.*, 48(11):1453-60 (2000) and Wadia and Stan, *Nat. Med.*, 10(3):310-5 (2004).

Other examples of molecules targeting extracellular matrix ("ECM") include glycosaminoglycan ("GAG") and collagen. In one embodiment, the external surface of a delivery vehicle or microparticle may be modified to enhance the ability of the microparticles to interact with selected cells or tissue. In another embodiment, the outer surface of a polymer microparticle having a carboxyl terminus may be linked to Pathogen-associated molecular patterns (PAMPs) that have a free amine terminus. The PAMP targets Toll-like Receptors (TLRs) on the surface of the cells or tissue, or signals the cells or tissue internally, thereby potentially increasing uptake. PAMPs may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

ii. Targeting Moieties

In some embodiments, compositions of cell penetrating anti-guanosine antibody or antigen binding fragment or fusions thereof include a targeting signal, a protein transduction domain or a combination thereof. The targeting moiety can be attached or linked directly or indirectly to the cell penetrating anti-guanosine antibodies. For example, in some embodiments, delivery vehicles used to deliver the cell penetrating anti-guano sine antibodies include targeting molecules. These can be coupled to the delivery vehicles using standard techniques. In some embodiments, the targeting moiety is attached or linked to a delivery vehicle such as a nanoparticle or a microparticle.

Targeting molecules can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques.

The targeting signal or sequence can be specific for a host, tissue, organ, cell, organelle, non-nuclear organelle, or cellular compartment. Moreover, the compositions disclosed here can be targeted to other specific intercellular regions, compartments, or cell types.

In one embodiment, the targeting signal binds to its ligand or receptor which is located on the surface of a target cell such as to bring the cell penetrating anti-guanosine antibody or antigen binding fragment or fusions thereof and cell membranes sufficiently close to each other to allow penetration of the antibody into the cell. Additional embodiments are directed to specifically delivering cell penetrating anti-guanosine antibody or antigen binding fragment or fusions thereof to specific tissue or cell types with cancer activity. In a preferred embodiment, the targeting molecule is an antibody or antigen binding fragment thereof, an antibody domain, an antigen, a T-cell receptor, a cell surface receptor, a cell surface adhesion molecule, a major histocompatibility locus protein, a viral envelope protein or a peptide selected by phage display that binds specifically to a defined cell.

Exemplary targeting signals include an antibody or antigen binding fragment thereof specific for a receptor expressed at the surface of a target cell or other specific antigens, such as cancer antigens.

Representative receptors include but are not limited to growth factors receptors, such as epidermal growth factor receptor (EGFR; HER1; c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-lreceptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor receptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

In some embodiments, the targeting signal also includes a protein transduction domain (PTD) or cell penetrating peptides (CPPS).

B. Pharmaceutical Compositions

The cell penetrating anti-guanosine antibody and antigen binding fragment and fusions thereof can be used therapeutically in combination with a pharmaceutically acceptable carrier. The materials may be in solution, emulsions, or suspension (for example, incorporated into microparticles, liposomes, or cells). Typically, an appropriate amount of a pharmaceutically-acceptable salt is used in the formulation to render the formulation isotonic. Examples of pharmaceutically-acceptable carriers include, but are not limited to, saline, Ringer's solution and dextrose solution. The pH of the solution is preferably from about 5 to about 8, and more preferably from about 7 to about 7.5. Pharmaceutical compositions may include carriers, thickeners, diluents, buffers, preservatives, and surface active agents. Further carriers include sustained release preparations such as liposomes, emulsions or depots. It will be apparent to those persons skilled in the art that certain carriers may be more preferable depending upon, for instance, the route of administration and concentration of composition being administered. Pharmaceutical compositions may also include one or more active ingredients such as antimicrobial agents, anti-inflammatory agents, anesthetics, and viscosity modifiers.

To aid dissolution of antibodies into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of peptides are for instance the fatty acids oleic acid, linoleic acid and linolenic acid.

The cell penetrating anti-guanosine antibody or antigen binding fragment or fusions thereof can be administered and taken up into the cells of a subject with or without the aid of a delivery vehicle. Appropriate delivery vehicles for the disclosed anti-guanosine antibodies are known in the art and can be selected to suit the particular anti-guanosine antibody or therapeutic target.

Micro and nanoparticles designed to deliver cargo such as drugs and antibodies to the vasculature, to organs or tissues are known in the art.

For example, perfluorocarbon nanoparticles, previously considered as artificial blood substitutes, have been developed into a platform technology for molecular imaging and targeted drug delivery, i.e., a so-called "theranostic" technology. These lipid-encapsulated particles, which are nominally 250 nm in diameter, can be administered intravenously and are typically constrained by size to the intact vasculature.

In some embodiments the delivery vehicle is a liposome. Liposomes are disclosed for the delivery of the cell-penetrating anti-guanosine antibodies directly to a certain target cell type, for example cancer cells. Target cells can internalize liposomes, leading to the delivery of the one or more cell penetrating anti-guanosine antibodies to the intracellular compartments of the target cell.

Suitable methods, materials and lipids for making liposomes are known in the art. Liposome delivery vehicles are commercially available from multiple sources. Liposomes can be formed from a single lipid bilayer (i.e., the liposome can be unilamellar) or several concentric lipid bilayers (i.e., the liposome can be multilamellar). The liposome may be formed from a single lipid; however, in some embodiments, the liposome is formed from a combination of more than one lipid. The lipids can be neutral, anionic or cationic at physiologic pH.

IV. Methods of Use

Methods of using the cell-penetrating anti-guanosine antibodies and antigen binding fragments and fusions thereof are provided. The cell-penetrating antibody or antigen binding fragment or fusions thereof can be administered to a subject with cells having mutant K-Ras in an amount effective to cause cytotoxicity in the cells having mutant K-Ras. Preferably the antibodies or antigen binding fragments or fusions thereof are selectively cytotoxic to cells having a mutation in K-Ras. For example, preferably the antibody or antigen binding fragment or fusions thereof are less toxic to cells without a mutation in K-Ras than to cells having a mutation in K-Ras. In the most preferred embodiments, the antibodies or antigen binding fragments or fusions thereof have little or even no toxicity to cells without a K-Ras mutation. The methods can include administering to a subject an effective amount of a composition including one or more cell penetrating anti-guanosine antibodies or antigen binding fragments or fusions thereof to prevent, reduce, or inhibit the growth of cancer cells in the subject. In preferred embodiments, the cell-penetrating antibodies or antigen binding fragments or fusions thereof are administered to a subject with cancer associated with mutant K-Ras in an amount effective to selectively cause cytotoxicity in cells having mutant K-Ras.

A. Methods of Treatment

Methods are provided for treating a disease or disorder associated with mutation in K-Ras in a subject by administering to the subject a therapeutically effective amount of cell-penetrating anti-guanosine antibody or antigen binding fragment or fusions thereof. For example, cell penetrating anti-guanosine antibodies or antigen binding fragments or fusions thereof can be used to specifically target and eliminate malignant cells with mutations in the K-Ras gene through either local or systemic delivery. In some embodiments, the disclosed compositions are administered systemically. Delivery vehicles can be selected and used to target the cell penetrating anti-guanosine antibody or antigen binding fragment or fusions thereof to a particular location or cell type. In other embodiments, the cell penetrating anti-guanosine antibodies or antigen binding fragments or fusions thereof are directly administered to a target tissue. In further embodiments, the route of administration targets the cell penetrating anti-guanosine antibodies or antigen binding fragments or fusions thereof directly to a specific organ or to tissue.

The compositions disclosed herein can reduce or prevent the growth of K-Ras mutant cancer cells, but allow the growth of tissue with wild-type K-Ras cells to occur. Exemplary K-Ras mutations include mutations in the K-Ras gene include mutations in codons 12, 13, and/or 61 that cause changes in amino acid content at positions 12, 13, and/or 61 in the K-Ras proteins. In some embodiments methods of treatment with the disclosed compositions selectively suppresses the growth of cells with mutant K-Ras, such as cancer cells. In some embodiments, the methods include suppressing the growth of cancer cells through a mechanism that is independent of necrosis or apoptosis. The methods can include suppressing the growth of cancer cells by inducing senescence specifically in cancer cells. In some embodiments, the methods involve first selecting a subject that has been identified as having mutant K-Ras. In a specific embodiment, the subject is diagnosed with a disease or disorder associated with mutant Ras, such as a cancer or tumor, or an infection with a pathogen such as a virus, or is identified as being at risk of developing a disease or disorder associated with mutant Ras, for example, subjects identified as having a nucleotide polymorphism in the H-Ras gene locus (81 Threonine>Cysteine) that has been associated with a higher risk of developing bladder carcinomas. Thus, the methods can include administering to a subject an effective amount of the cell-penetrating anti-guanosine antibody, or fragments or variants thereof, to reduce one or more symptoms of cancer, for example, tumor burden.

Methods of treatment and prevention of diseases and disorders using the cell-penetrating anti-guanosine antibodies or antigen binding fragments or fusions thereof optionally including a delivery vehicle are discussed in more detail below.

1. Controls

The effect of a cell penetrating anti-guanosine antibody or antigen binding fragment or fusion thereof can be compared to a control. Suitable controls are known in the art and include, for example, untreated cells or an untreated subject. In some embodiments, the control is untreated tissue from the same subject that is treated, or from a different, untreated subject. Preferably the cells or tissue of the control are derived from the same tissue as the treated cells or tissue. In some embodiments, an untreated control subject suffers from the same disease or condition as the treated subject. For example, in some embodiments, one or more of the pharmacological or physiological markers or pathways affected by cell penetrating anti-guanosine antibody or antigen binding fragments or fusions thereof is compared to the same pharmacological or physiological marker or pathway in untreated control cells or untreated control subjects. In some embodiments, cell penetrating anti-guanosine antibody-treated subjects are compared to subjects treated with other antineoplastic drugs, such as alkylating agents, antimetabolites, anthracyclines, plant alkaloids, topoisomerase inhibitors, monoclonal antibodies, or other anti-tumor agents. The subjects treated with other antineoplastic drugs can have a greater incidence of toxic side effects or proliferation of cancer cells than do subjects treated with the cell penetrating anti-guanosine antibodies or antigen binding fragments or fusions thereof.

2. Dosage Regimens, Route of Administration

Pharmaceutical compositions including one or more cell penetrating anti-guanosine antibodies or antigen binding fragments or fusions thereof can be administered in a variety of manners, depending on whether local or systemic treatment is desired, and depending on the area to be treated. For example, the disclosed compositions can be administered intravenously, intraperitoneally, intramuscularly, subcutaneously, or intracavity.

In certain embodiments, the compositions are administered locally, for example by injection directly into a site to be treated. Local delivery of drugs can reduce side effects or toxicity associated with systemic delivery and can result in enhanced treatment outcome due to an increased localized dose.

In certain embodiments cell penetrating anti-guanosine antibodies or antigen binding fragments or fusions thereof can be administered directly to a treated tissue, such as a tumor, without engendering adverse systemic effects. In further embodiments, the compositions are injected or otherwise administered directly to one or more surgical sites. Typically, local injection causes an increased localized concentration of the compositions which is greater than that which can be achieved by systemic administration. In preferred embodiments, the compositions are delivered directly to tissue by local administration.

Cell penetrating anti-guanosine antibodies or antigen binding fragments or fusions thereof can be administered during a period before, during, or after onset of disease symptoms, or any combination of periods before, during or after onset of one or more disease symptoms. In some embodiments, the cell penetrating anti-guanosine antibodies or antigen binding fragments or fusions thereof is administered to a subject once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the frequency of administration is once weekly, or is once every two weeks, or is once every four weeks, or is twice every week. For example, the subject can be administered one or more doses of the composition every 1, 2, 3, 4, 5, 6 7, 14, 21, 28, 35, or 48 days prior to onset of disease symptoms. The subject can be administered one or more doses of the composition every 1, 2, 3, 4, 5, 6, 7, 14, 21, 28, 35, or 48 days after the onset of disease symptoms. In some embodiments, the multiple doses of the compositions are administered before an improvement in disease condition is evident. For example, in some embodiments, the subject receives 1, 2, 3, 4, 5, 6 7, 14, 21, 28, 35, or 48 dose, over a period of 1, 2, 3, 4, 5, 6 7, 14, 21, 28, 35, or 48 days or weeks before an improvement in the disease or condition is evident. The frequency of administration can be, for example, one, two, three, four or more times daily, weekly, every two weeks, every three weeks, or monthly The compositions including one or more cell penetrating anti-guanosine antibodies or antigen binding fragments or fusions thereof can be administered at different times in relation to a diagnosis, prognosis or surgery, depending on the cancer to be treated. The timing of commencement of cell penetrating anti-guanosine antibody therapy should be determined based upon the needs of the subject, and can vary from at the time of diagnosis or procedure, such as radiotherapy, surgery or other chemotherapy, to one or more days, weeks or months after a diagnosis or procedure. In some embodiments, therapy using cell penetrating anti-guanosine antibodies can be discontinued once cancer-tissue cytotoxicity has occurred.

3. Effective Amounts

It may be that cell penetrating anti-guanosine antibodies or antigen binding fragments or fusions thereof perturb intracellular G-protein coupled signaling events and inhibit, reduce, or otherwise alter multiple G-protein mediated cell-signaling pathways. For example, cell-penetrating anti-guanosine antibodies or antigen binding fragments or fusions thereof can inhibit, reduce or otherwise alter the phosphorylation of intracellular kinase molecules, including, but not limited to, PKA, PKC and Rho kinase and can inhibit, reduce or otherwise alter the phosphorylation of intracellular signaling molecules, including, but not limited to, protein kinase B (PKB; Akt), extracellular-regulated kinase (ERK), mammalian target of rapamycin (mTOR), p70S6k.

In some in vivo approaches, the compositions of cell penetrating anti-guanosine antibody or antigen binding fragments or fusions thereof are administered to a subject in a therapeutically effective amount. In some embodiments, the pharmaceutical composition is a unit dosage containing one or more cell penetrating anti-guanosine antibodies or antigen binding fragments or fusions thereof in a pharmaceutically acceptable excipient, wherein one or more antibodies is present in an amount effective to cause cytotoxicity in a cancer cell with mutant K-Ras.

In certain embodiments, cell-penetrating anti-guanosine antibodies or antigen binding fragments or fusions thereof are present in an amount effective to reduce the amount of phosphorylated ERK (p-ERK) and phosphorylated Akt (p-Akt) without affecting the total amount of intracellular ERK and Akt. Preferably, the reduction in p-Akt and p-ERK is sufficient to cause cytotoxicity in cells harboring mutations in the small GTPase K-Ras but does not cause cytotoxicity in cells with wild-type K-Ras.

In preferred embodiments, the amount of the cell-penetrating anti-guanosine antibodies or antigen binding fragments or fusions thereof is effective to kill 100%, 99% or greater than 90% of K-Ras mutant cells. More preferably the same amount of the cell-penetrating anti-guanosine antibodies or antigen binding fragments or fusions thereof causes minimal cytoxicity in cells with wild-type K-Ras.

In some embodiments, the unit dosage is in a unit dosage form for intravenous injection. In some embodiments, the unit dosage is in a unit dosage form for oral administration. In some embodiments, the unit dosage is in a unit dosage form for intra-tumoral injection.

For all of the disclosed compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

Generally dosage levels of between 0.001 and 100 mg/kg of body weight daily are administered to mammals, most preferably, humans. Generally, for intravenous injection or infusion, dosage may be lower. Preferably, the compositions are formulated to achieve a cell penetrating anti-guanosine antibody serum level of between about 1 and about 1000 µM.

In some embodiments the cell penetrating anti-guanosine antibodies or antigen binding fragments or fusions thereof induce replicative or cellular senescence in cancer cells. Senescence is a process leading to irreversible arrest of cell division which was first described in cultures of human fibroblasts that lost the ability to divide upon continuous subculture (Hayflick, *Exp. Cell Res.*, 37:614-636 (1965)). Since then, replicative senescence has been shown in various mammalian tissues in culture and in vivo (Dimri, et al., *Proc. Natl. Acad. Sci. USA*, 92:9363-9367 (1995); Stanulis-Praeger, et al., *Mech. Ageing Dev.*, 38:1-48 (1987)). Contrary to normal somatic cells, most tumors have extended or infinite life spans. Cellular and viral oncogenes, or the loss of tumor suppressors, are involved in the transformation and immortalization of primary cells. Inactivation of the p53 and p16INK4a tumor suppressors is among the most common events in human cancers. Therefore, in some embodiments one or more cell penetrating anti-guanosine antibodies or antigen binding fragments or fusions thereof are in an amount effective to induce senescence in cancer cells in a subject compared to an untreated control.

4. Diseases to be Treated i. Malignancies Associated with Mutant K-Ras

Cell penetrating anti-guanosine antibodies or antigen binding fragments or fusions thereof have a wide variety of therapeutic and prophylactic anti-cancer uses. For example, antibody 4H2, or antigen binding molecules thereof can be used to treat, reduce, and/or prevent one or more symptoms of cancer in a subject. The effective amount or therapeutically effective amount of the antigen binding molecule to treat cancer or a tumor thereof is typically a dosage sufficient to reduce or prevent a least one symptom of the cancer, or to otherwise provide a desired pharmacologic and/or physiologic effect. The symptom may be physical, such as tumor burden, or biological such as reducing proliferation or increasing death of cancer cells. In some embodiments, the amount is effective to kill tumor cells or reduce or inhibit proliferation or metastasis of the tumor cells. In some embodiments, the amount is effective to reduce tumor burden. In some embodiments, the amount is effective to reduce or prevent at least one co-morbidity of the cancer.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer typically refers to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated can be classified according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

Cell penetrating anti-guanosine antibodies or antigen binding fragments or fusions thereof can be used to treat cells undergoing unregulated growth, invasion, or metastasis.

Tumor cell hypoxia is now recognized as a problem in cancer therapy because it makes cancer cells resistant to treatment with radiation and some chemotherapeutics. Hypoxia is also known to cause impaired DNA repair in cancer cells. Accordingly, in some embodiments, the disclosed active agents are used as targeted agents for hypoxic tumor cells.

Therapeutically effective amounts of cell-penetrating anti-guanosine antibodies, or fragments or variants thereof, used in the treatment of cancer will generally kill tumor cells or inhibit proliferation or metastasis of the tumor cells. In preferred embodiments, one or more cell penetrating anti-guanosine antibodies or antigen binding fragments or fusions thereof are effective to prevent, reduce, inhibit, or delay one or more symptoms of a cancer in a subject. Symptoms of cancer may be physical, such as tumor burden, or biological such as proliferation of cancer cells.

Cells undergoing unregulated growth, invasion, or metastasis are generally referred to as cancerous, neoplastic or transformed cells. Typically, the growth of a cancerous or neoplastic cell exceeds and is not coordinated with that of the normal, non-cancerous tissues around it. The growth can persist in the same excessive manner even after cessation of a pro-proliferative stimuli, and typically causes formation of a tumor. Neoplasms may be benign, pre-malignant or malignant.

Cancerous cells can develop as a result of somatic, gain-of-function mutations in Ras genes, resulting in activating mutations in small GTPase Ras enzymes. Oncogenic mutations of the H-Ras, N-Ras, or K-Ras genes are most frequently associated with malignancies in humans. In certain embodiments, the cells express a mutant form of the small GTPase Ras family, such as K-Ras. In certain embodiments the cells do not express the wild type Ras genes.

Oncogenic mutations have also been identified in other upstream or downstream components of the Ras intracellular signaling pathways, including cytosolic kinases and membrane RTKs (Ras/MAPK pathways).

Oncogenic mutations in the K-Ras gene can result in constitutive activation of the out-coming Ras proteins.

Exemplary mutations include mutations in codons 12, 13, and/or 61 that result in any changes in the amino acids occurring at positions 12, 13, or 61 of the K-ras protein. This includes for example but is not limited to K-ras amino acid 12 (changing glycine to aspartic acid, cysteine, serine, threonine, arginine, or valine) and amino acid 13 and 61 (changing glutamine to lysine, arginine, leucine, or aspartic acid). Another way of describing these K-Ras mutations that are exemplary in this context is G12A, G12C, G12D, G12S, G12I, G12R, G12V, G13C, G13D, G13S, Q61L, Q61R. Again, any change in amino acid content at positions 12, 13, 61 are considered exemplary mutations.

Methods of using one or more cell penetrating anti-guanosine antibodies or antigen binding fragments or fusions thereof for treating a cancer characterized by deregulation of Ras-dependent signaling are provided. In preferred embodiments the cancer is characterized by the mutation of one or more Ras genes or mutation of genes encoding other components of Ras/MAPK signaling pathways. The antibodies can be used to treat cells undergoing unregulated growth, invasion, or metastasis including, but not limited to, pancreatic ductal adenocarcinoma, colorectal carcinoma, non-small cell lung carcinoma (NSCLCS), malignant melanoma, urinary bladder carcinoma, thyroid carcinomas, hematopoietic malignancies, breast cancer, hepatocellular carcinomas, prostate cancer, biliary tract adenocarcinomas, angiosarcomas, malignant fibrous histiocytoma, neuroblastomas, cervix adenocarcinomas, or stomach cancers and neck and head cancer, bowel cancer.

Methods of using one or more cell penetrating anti-guanosine antibodies or antigen binding fragments or fusions thereof for treating a cancer characterized by the proliferation of cells having gain-of-function mutations in the K-Ras gene are described. The antibodies can be used to treat cells undergoing unregulated growth, invasion, or metastasis including, but not limited to, breast cancer, ovarian cancer and prostate cancer.

iii. Other Malignancies

The cell penetrating anti-guanosine antibodies or antigen binding fragments or fusions thereof can be used alone, or in combination with radiotherapy, chemotherapy, or any combination thereof, to treat any cancer, including carcinomas, gliomas, sarcomas, or lymphomas.

A representative but non-limiting list of cancers that the disclosed compositions can be used to treat include cancers of the blood and lymphatic system (including leukemias, Hodgkin's lymphomas, non-Hodgkin's lymphomas, solitary plasmacytoma, multiple myeloma), cancers of the genitourinary system (including prostate cancer, bladder cancer, renal cancer, urethral cancer, penile cancer, testicular cancer), cancers of the nervous system (including mengiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer), and pediatric cancers (including neuroblastoma, Ewing's sarcoma, Wilms tumor, medulloblastoma).

In some embodiments, the cancer is a neoplasm or tumor that demonstrates some resistance to radiotherapy or chemotherapy. Cancers that are resistant to radiotherapy using standard methods include sarcomas, lymphomas, leukemias, carcinomas, blastomas, and germ cell tumors.

B. Combination Therapies

The disclosed compositions including cell penetrating anti-guanosine antibodies or antigen binding fragments or fusions thereof can be administered alone, or in combination with one or more additional active agent(s), or treatment processes as part of a therapeutic or prophylactic treatment regime.

1. Additional Therapeutic Agents

In some embodiments compositions including one or more cell penetrating anti-guanosine antibodies or fragments thereof are administered in combination with one or more additional therapeutic agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second).

For example, the composition can be administered on the first, second, third, or fourth day, or combinations thereof. The composition can be administered on the same day, or a different day than the one or more additional active agents.

The additional therapeutic agents can be chemotherapeutic drugs including, but not limited to, alkylating agents, antimetabolites, anthracyclines, plant alkaloids, topoisomerase inhibitors, monoclonal antibodies, and other anti-tumor agents.

In some embodiments, the additional therapeutic agents are antineoplastic drugs that damage DNA or interfere with DNA repair. These antineoplastic drugs can synergize effectively with the cell penetrating anti-guanosine antibodies. In these embodiments, the antibody increases the cell's sensitivity to the chemotherapy by at least 10%, 15%, 20%, 25%, 30%, 35%, 40%, 45%, 50%.

Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas. Examples of antineoplastic drugs that can be combined with the cell-penetrating anti-guanosine antibodies include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), anti-mitotics (including taxanes such as paclitaxel and decetaxel, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide).

In a particular embodiment, the antineoplastic drug is an inhibitor of the enzyme poly ADP ribose polymerase (PARP inhibitor), which inhibits a step in base excision repair of DNA damage. In some embodiments, the additional antineoplastic drug is a histone deacetylase inhibitor, which suppresses DNA repair at the transcriptional level and disrupt chromatin structure.

In other embodiments, one or more additional antineoplastic drugs complement the anti-guanosine antibodies by targeting a different activity in the cancer cell. In these embodiments, the antineoplastic drug does not inhibit intracellular phosphorylation.

In further embodiments, the additional active agents can be other antibodies. The other antibodies can be cell penetrating antibodies, such as the anti-DNA antibody 3E10 or 5C6. Monoclonal antibody 3E10 and 3E10 Fv, without being conjugated to any therapeutic protein, enhances cancer cell radio-sensitivity and chemo-sensitivity and this effect is potentiated in cells deficient in DNA repair, as described in PCT/US2012/31860.

In specific embodiments, the additional active agents can be specific monoclonal antibodies against the epidermal growth factor receptor (EGFR; ErbB-1; HER1 in humans) such as cetuximab and panitumumab. In other embodiments, the additional active agents can be additional combinations of anti-EGFR Mab-based therapies, or alternative therapeutic approaches such as vaccines against mutant K-Ras, and/or inhibitors of other downstream kinases.

In yet further embodiments, the additional active agents can be antibiotics, antivirals, steroidal and non-steroidal anti-inflammatories, conventional immunotherapeutic agents, immune-suppressants, cytokines, chemokines and/or growth factors, anti-proliferatives or anti-migration agents.

2. Radiotherapy

In some embodiments compositions including one or more cell penetrating anti-guanosine antibodies or antigen binding fragments or fusions thereof are administered in combination with radiotherapy. Radiation therapy (radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. In some embodiments, anti-guanosine antibodies are used to increase sensitivity to radiotherapy (radiosensitivity) for a non-malignant condition.

Radiation therapy works by damaging the DNA of dividing cells, e.g., cancer cells. This damage is either direct or indirect. Indirect ionization happens as a result of the ionization of water, forming free radicals, notably hydroxyl radicals, which then damage the DNA. Direct damage to cancer cell DNA occurs through high-LET (linear energy transfer) usually causing double-stranded DNA breaks.

The amount of radiation used in photon radiation therapy is measured in Gray (Gy), and varies depending on the type and stage of cancer being treated. For curative cases, the typical dose for a solid epithelial tumor ranges from 60 to 80 Gy, while lymphomas are treated with 20 to 40 Gy. Postoperative (adjuvant) doses are typically around 45-60 Gy in 1.8-2 Gy fractions (for breast, head, and neck cancers).

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radio-resistant, that is, much higher doses are required to produce a radical cure than may be safe in clinical practice. Renal cell cancer and melanoma are generally considered to be radio-resistant.

In some embodiments, the cell-penetrating anti-guanosine antibodies or antigen binding fragments or fusions thereof serve the function of enhancing the radiosensitivity of cancers. In these embodiments, the cell-penetrating anti-guanosine antibodies increase the cell's sensitivity to the radiotherapy by at least 10%, 15%, 20%, 25%, 30%, 35%, 40%, 45%, 50%. Moreover, the cell-penetrating anti-guanosine antibodies can be combined with one or more additional radiosensitizers. Examples of known radiosensitizers include cisplatin, gemcitabine, 5-fluorouracil, pentoxifylline, and vinorelbine.

The present invention will be further understood by reference to the following non-limiting examples.

EXAMPLES

Example 1: 4H2 is a Lupus Autoantibody that Penetrates into Cells and does not Localize to the Nucleus Materials and Methods
Hybridomas and Cell Lines The 4H2 hybridoma cell line previously generated from the MRLmpj/lpr lupus mouse model and nucleoside binding activity was evaluated (Zack, et al., *J. Immunol.* 154:1987-1994 (1995); Gu, et al., *J. Immunol.*, 161:6999-7006 (1998)). The 4H2 monoclonal antibody (mAb 4H2) was purified from cell culture using standard techniques.

Cell-Penetration Assays

To demonstrate the ability of mAb 4H2 to penetrate into cells and to determine whether mAb 4H2 localizes to nucleus, a matched pair of Cal12T lung cancer cell lines with and without an activating K-ras mutation (G12C) were stained with 4H2, followed by immune-staining for IgG. The matched pair of Cal12T cell lines were treated with 4H2 (1.5 mg/mL) for one hour and washed, followed by fixation and immunofluorescence with an Alexa488-conjugated antibody against mouse IgG. Propidium iodide (PI) staining was performed to allow visualization of cell nuclei. The location of mAb 4H2 inside cells was identified as green fluorescence, as compared to PI nuclear stain in red.

Results

A panel of lupus autoantibodies from the MRL-mpj/lpr mouse model of SLE previously established (Zack, et al., *J. Immunol.* 154:1987-1994 (1995)), was screened. This panel includes cell-penetrating anti-guanosine antibody clone 4H2.

4H2 penetrated into both K-Ras mutant and non-mutant Cal12T cell lines PI counterstaining allowed direct visualization of cell nuclei, and overlay of anti-IgG and PI fluorescent images confirmed 4H2 was localized to the cytoplasm outside of the cell nucleus in both cell lines.

Example 2: 4H2 Inhibits Phosphorylation of ERIC and Akt

Materials and Methods
p-ERK and p-Akt Assays

The effects of 4H2 upon G-protein associated intracellular signaling were assessed by examining the impact of 4H2 on the amounts of phospho-ERK (p-ERK) and phospho-Akt (p-Akt) in Cal12T cells. Cal12T lung cancer cells were treated with 4H2 for 4 hours. Cell lysates were then subjected to Western blot analysis to determine amounts of total ERK, p-ERK, total Akt, and p-Akt.

Results

To test the hypothesis that 4H2 interferes with G-protein associated intracellular signaling, the impact of 4H2 on the amounts of phospho-ERK (p-ERK) and phospho-Akt (p-Akt) in Cal12T was examined.

Total amounts of ERK and Akt did not appear to be changed by 4H2 treatment, but amounts of p-ERK and p-Akt were reduced in the cells treated with 4H2. Thus, 4H2 did not have any significant impact on total amounts of ERK and Akt, but a distinct reduction in the amount of p-ERK and p-Akt was observed. This finding is consistent with the concept that 4H2 perturbs intracellular signaling pathways associated with G-proteins.

Example 3: 4H2 is Toxic to Cancer Cells with Mutant K-RAS

Materials and Methods
Colony Formation Assays

The toxicity of mAb 4H2 to cells that are dependent on aberrant G-protein signaling for proliferation and survival was assessed.

A549 lung cancer cells that harbor a G12S activating K-Ras were treated with control buffer or 1.5 mg/mL 4H2, and the cells were evaluated by colony formation assay, as described by Hansen, et al., Sci Transl Med., 4(157) (2012.).

Results

The effect of 4H2 on the clonogenic survival of the Cal12T cells was established using the colony formation assay. 4H2 had a significant toxic effect on the clonogenic survival of the K-Ras mutant cells relative to control cells.

4H2 reduced the surviving fraction of the A549 cells to 0.29±0.08 (p=0.04). Results are illustrated in FIG. 1.

Example 4: 4H2 is Selectively Toxic to Cal12T Cells with a G12C K-RAS Mutation Materials and Methods
Cytotoxicity Assays To determine if 4H2 is equally toxic to cells without a K-Ras mutation or if it is selectively toxic K-Ras mutant cancer cells isogenic matched pairs of Cal12T lung cancer cells with and without a G12C activating K-Ras mutation and SW48 colon cancer cells with and without a G12A activating K-Ras mutation were obtained. Matched pairs of cells were treated with control buffer or 4H2 (0-0.5 mg/mL) and evaluated by colony formation assay. Surviving fractions relative to control cells are presented.

Results

4H2 was significantly toxic to the K-Ras mutant Cal12T cells, but spared the K-Ras WT Cal12T cells. 4H2 was similarly toxic to the K-Ras mutant SW48 cells but spared the WT SW48 cells.

Figure 2:
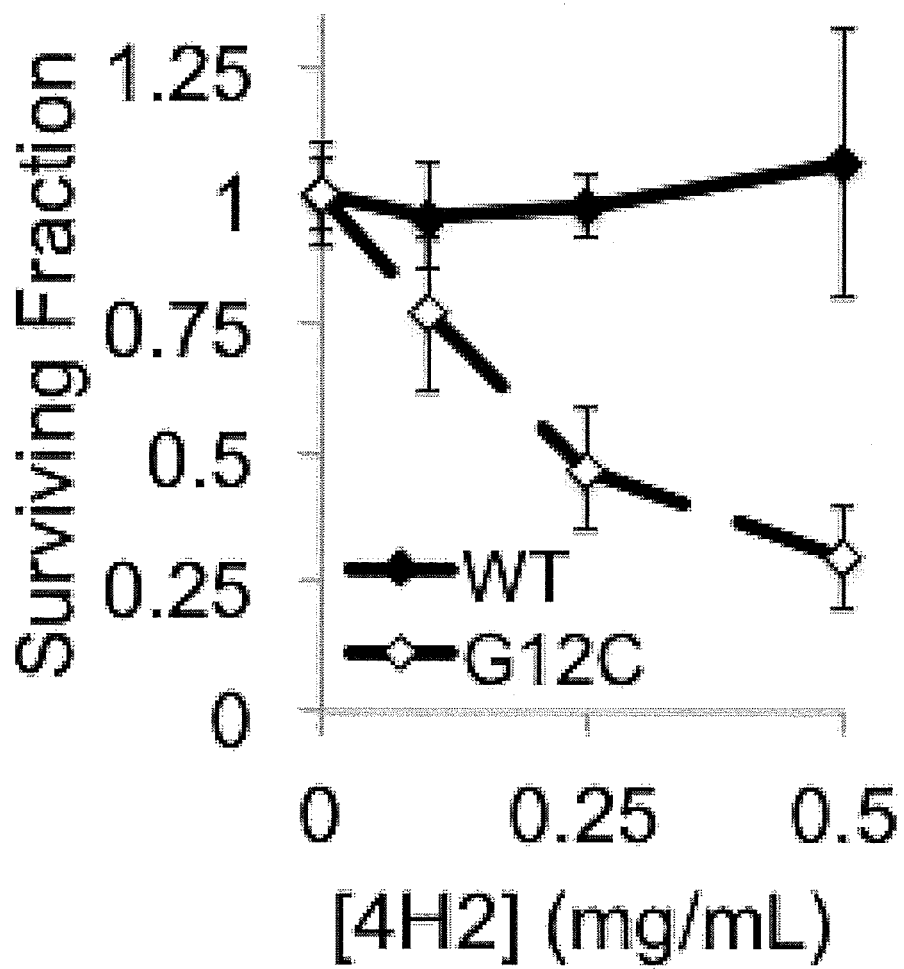
FIG. 2 is a line graph showing the surviving fraction of Cal12T cells without (WT; ♦) and with the G12C mutation in K-Ras (G12C; ◊), respectively, following exposure to varied concentrations (0 to 0.5 mg/ml) of mAb 4H2, as compared to control cells.

These cytotoxicity assays demonstrated that 4H2 is not significantly toxic to cells with WT K-Ras, however 4H2 is significantly toxic to cells with mutant K-Ras. Results are illustrated in FIG. 2.

Summary

The data establish that the cell-penetrating lupus anti-guanosine antibody 4H2 reduces phosphorylation of ERK and Akt in cells, is toxic to cancer cells harboring a range of mutations in the small GTPase K-Ras (including G12S, G12C, G12A), and is not significantly toxic to cells with WT K-Ras. These observations establish that 4H2 penetrates cells and inhibits phosphorylation of ERK and Akt, and that cells with preexisting activating mutations in K-Ras are more sensitive to this inhibition than cells with WT K-Ras. A wide range of human malignancies harbor deficiencies in the small GTPase K-Ras (Adjei, J Natl Cancer Inst 93 (14): 1062-1074 (2001)), and this therapeutic strategy therefore has potential for applications in the selective treatment of numerous tumors. These findings demonstrate the potential utility of 4H2 in targeted therapy for K-Ras associated malignancies and strengthen the rationale for studies of additional lupus autoantibodies in order to identify the best candidates for development as therapeutic agents. Further, the cytotoxic effect of 4H2 on K-Ras mutant cells provides support for the hypothesis that some lupus autoantibodies contribute to the unusual cancer risk profile associated with systemic lupus erythematosus.

We claim:

1. A method of treating cancer comprising administering to a subject with a cancer comprising cells with one or more K-Ras gene mutations an effective amount of a cell-penetrating anti-guanosine antibody or an antigen binding fragment thereof or fusion protein comprising
    a heavy chain variable region comprising sequentially the first, second, and third complementarity determining regions (CDRs) of SEQ ID NO:5, and
    a light chain variable region comprising sequentially the first, second, and third CDRs of SEQ ID NO:1.

2. The method of claim 1, wherein the antibody or antigen binding fragment thereof or fusion protein is in a pharmaceutical composition comprising a sterile pharmaceutically acceptable excipient for administration to a human.

3. The method of claim 2, wherein the antibody or antigen binding fragment thereof is present in a dosage unit in an amount from about 0.01 to about 100 mg/kg body weight of a human.

4. The method of claim 1, wherein the antibody or antigen binding fragment thereof or fusion protein inhibits or reduces phosphorylation of ERK and/or Akt in a cell as compared to an untreated control cell.

5. The method of claim 1, wherein the antibody or antigen binding fragment thereof or fusion protein causes cytotoxicity to cells having one or more amino acid mutations in the small GTPase K-Ras.

6. The method of claim 1, wherein the cell-penetrating anti-guanosine antibody is monoclonal antibody 4H2 or an antigen binding fragment thereof.

7. The method of claim 1, further comprising administering the subject one or more antineoplastic or radiosensitizing agents selected from the group consisting of cisplatin, cytoxan, doxorubicin, methotrexate, mitomycin c, nitrogen mustard, hydroxyurea, bevacizumab, cetuximab, rituximab, trastuzumab tirapazamine, temozolomide, camptothecin, cisplatin, gemcitabine, 5-fluorouracil, hydroxyurea, pentoxifylline, vinorelbine, and combinations thereof.

8. The method of claim 2, wherein the pharmaceutical composition is in a unit dosage form for intravenous injection or intra-tumoral injection.

9. The method of claim 1, wherein the antibody or antigen binding fragment or fusion protein is a humanized form of monoclonal antibody 4H2 or an antigen binding fragment thereof.

10. The method of claim 6, wherein the antigen binding fragment of monoclonal antibody 4H2 comprises a single chain variable fragment (scFv).

11. The method of claim 9, wherein the antigen binding fragment binds to the same epitope as monoclonal antibody 4H2.

12. The method of claim 1, wherein the antibody, or antigen binding fragment thereof or fusion protein is administered to the subject in an amount effective to inhibit or reduce one or more symptoms of the cancer.

13. The method of claim 1, wherein the cancer is selected from the group consisting of pancreatic ductal adenocarcinoma, colorectal carcinoma, nonsmall cell lung carcinoma (NSCLCS), small cell lung cancer, malignant melanoma, urinary bladder carcinoma, thyroid carcinomas, hematopoietic malignancies, breast cancer, hepatocellular carcinomas, prostate cancer, biliary tract adenocarcinomas, angiosarcomas, malignant fibrous histiocytoma, neuroblastomas, cervix adenocarcinomas, stomach cancers and neck and head cancer, bowel cancer and pediatric cancers.

14. The method of claim 13, wherein the cancer is resistant to radiotherapy.

15. The method of claim 13, wherein the cancer is resistant to chemotherapy.

16. The method of claim 1, wherein the cancer is characterized by an activating mutation in the small GTPase K-RAS.

17. The method of claim 16, wherein the subject has been diagnosed with one or more mutations in the small GTPase K-Ras gene causing changes in amino acids at position 12, 13, 61, or a combination thereof in the K-Ras protein.

18. The method of claim 1, further comprising treating the subject with radiation therapy or chemotherapy, wherein the pharmaceutical composition increases the cell's sensitivity to radiation therapy or chemotherapy.

19. The method of claim 18, wherein the antibody, or an antigen binding fragment thereof or fusion protein is administered to the subject at least 24 hours before the radiation therapy or chemotherapy, is administered to the subject concurrently with radiation therapy or chemotherapy, or is administered to the subject within 24 hours after radiation therapy or chemotherapy.

20. The method of claim 1, wherein the cell-penetrating anti-guanosine antibody is transported into the cytoplasm of the cell without the aid of a carrier or conjugate.

21. The method of claim 1, wherein the
light chain variable region comprises SEQ ID NO:1 or a humanized form thereof; and
the heavy chain variable region comprises SEQ ID NO:5 or a humanized form thereof.

22. The method of claim 21, wherein the light chain variable region comprises SEQ ID NOS:2, 3, and 4 and the heavy chain variable region comprises SEQ ID NOS:6, 7, and 8.

23. The method of claim 22, wherein the antibody or antigen binding fragment thereof is a humanized antibody or antigen binding fragment thereof comprising SEQ ID NOS: 2, 3, and 4 and SEQ ID NOS:6, 7, and 8.

24. The method of claim 22, wherein the antibody or antigen binding fragment thereof is a single chain variable fragment (scFv).

25. The method of claim 1, wherein the antibody or antigen binding fragment thereof or fusion protein is administered to the subject in an amount effective to reduce or inhibit the growth or proliferation of cells having one or more amino acid mutations in the small GTPase K-Ras.

26. The method of claim 1, wherein the light chain variable region comprises SEQ ID NO:1 and the heavy chain variable region comprises SEQ ID NO:5.

27. The method of claim 1, wherein the antibody or antigen binding fragment thereof or fusion protein is a humanized antibody or an antigen binding fragment thereof.

28. The method of claim 1, wherein the antibody or antigen binding fragment thereof, or fusion protein is a chimeric antibody.

29. The method of claim 28, wherein
the first light chain CDR comprises the amino acid sequence of SEQ ID NO:2;
the second light chain CDR comprises the amino acid sequence of SEQ ID NO:3;
the third light chain CDR comprises the amino acid sequence of SEQ ID NO:4;
the first heavy chain CDR comprises the amino acid sequence of SEQ ID NO:6;
the second heavy chain CDR comprises the amino acid sequence of SEQ ID NO:7; and
the third heavy chain CDR comprises the amino acid sequence of SEQ ID NO:8.

30. A method of treating cancer, comprising administering to a subject with a cancer comprising cells with one or more K-Ras gene mutations an effective amount of a cell-penetrating anti-guanosine antibody or an antigen binding fragment thereof or fusion protein comprising
a heavy chain variable region comprising sequentially the first, second, and third complementarity determining regions (CDRs) and an amino acid sequence at least 85% identical to the amino acid sequence of SEQ ID NO:5, and
a light chain variable region comprising sequentially the first, second, and third CDRs and an amino acid sequence at least 85% identical to the amino acid sequence of SEQ ID NO:1.

31. The method of claim 30, wherein the antibody or antigen binding fragment thereof or fusion protein is a humanized antibody or an antigen binding fragment thereof.

32. The method of claim 30, wherein the antibody or antigen binding fragment thereof, or fusion protein is a chimeric antibody.

33. The method of claim 30, wherein the antibody or antigen binding fragment thereof, or fusion protein comprises a single chain variable fragment (scFv).

34. The method of claim 30, wherein the cancer is characterized by an activating mutation in the small GTPase K-RAS.

35. The method of claim 34, wherein the subject has been diagnosed with one or more mutations in the small GTPase K-Ras gene causing changes in amino acids at position 12, 13, 61, or a combination thereof in the K-Ras protein.

* * * * *